United States Patent [19]

He et al.

[11] Patent Number: 6,110,520

[45] Date of Patent: Aug. 29, 2000

[54] PROCESS FOR PREPARING GAMM-HEXALACTONE, PRODUCTS PRODUCED THEREFROM DAN ORGANOLEPTIC USES OF SAID PRODUCTS

[75] Inventors: Fenjin He; Mohamad I. Farbood, both of State College, Pa.; Laura E. Kizer, Highlands, N.J.

[73] Assignee: International Flavors & Fragrances Inc., New York, N.Y.

[21] Appl. No.: 09/275,768

[22] Filed: Mar. 25, 1999

[51] Int. Cl.$^7$ .................................................. A23L 1/22
[52] U.S. Cl. ........................ 426/536; 435/125; 435/126; 435/146; 435/148; 435/171.1; 435/254.1; 435/256.1; 435/911; 435/913; 435/918; 549/295; 549/326; 424/48; 424/76.1; 424/76.4; 424/65; 426/650; 510/103; 510/518; 512/11
[58] Field of Search ...................................... 435/125, 126, 435/146, 148, 171, 254.1, 256.1, 911, 913, 918; 549/295, 326; 512/11; 424/48, 76.4, 76.1, 65; 106/31.02; 510/103, 518; 426/536, 650

[56] References Cited

U.S. PATENT DOCUMENTS

| | | | |
|---|---|---|---|
| 5,032,513 | 7/1991 | Page et al. | 435/125 |
| 5,166,366 | 11/1992 | Farbood et al. | 549/273 |
| 5,274,128 | 12/1993 | Farbood et al. | 549/295 |
| 5,763,233 | 6/1998 | Gocho et al. | 435/125 |

*Primary Examiner*—Herbert J. Lilling
*Attorney, Agent, or Firm*—Arthur L. Liberman

[57] ABSTRACT

A process for producing high yields of γ-hexalactone and 2-pentanone from the corresponding hexanoic acid starting material is carried out with high amounts of oxygen and sugar in the presence of a mold microorganism. Fragrance compositions and foodstuff compositions are augmented and enhanced by the presence of the product compounds.

27 Claims, 18 Drawing Sheets

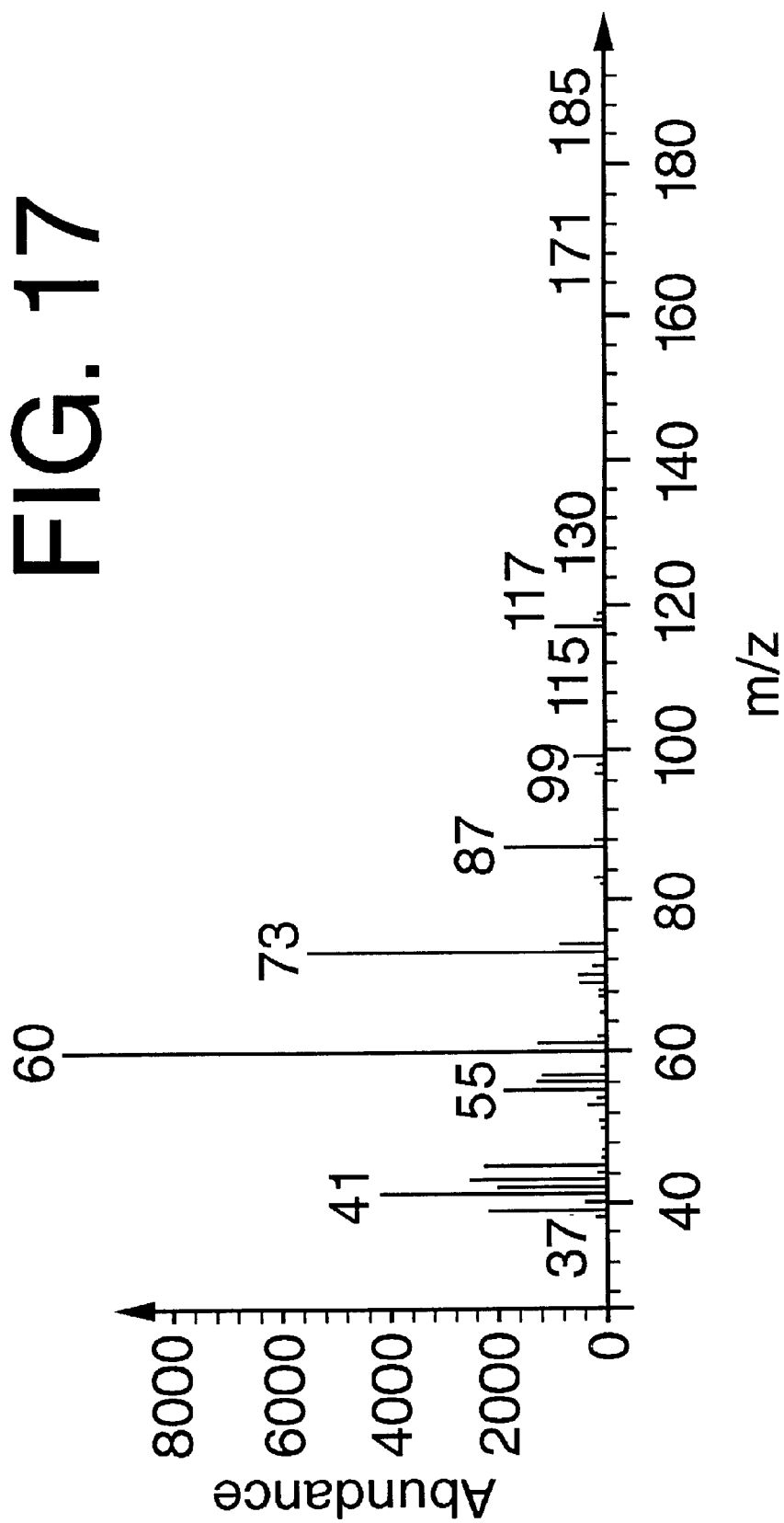

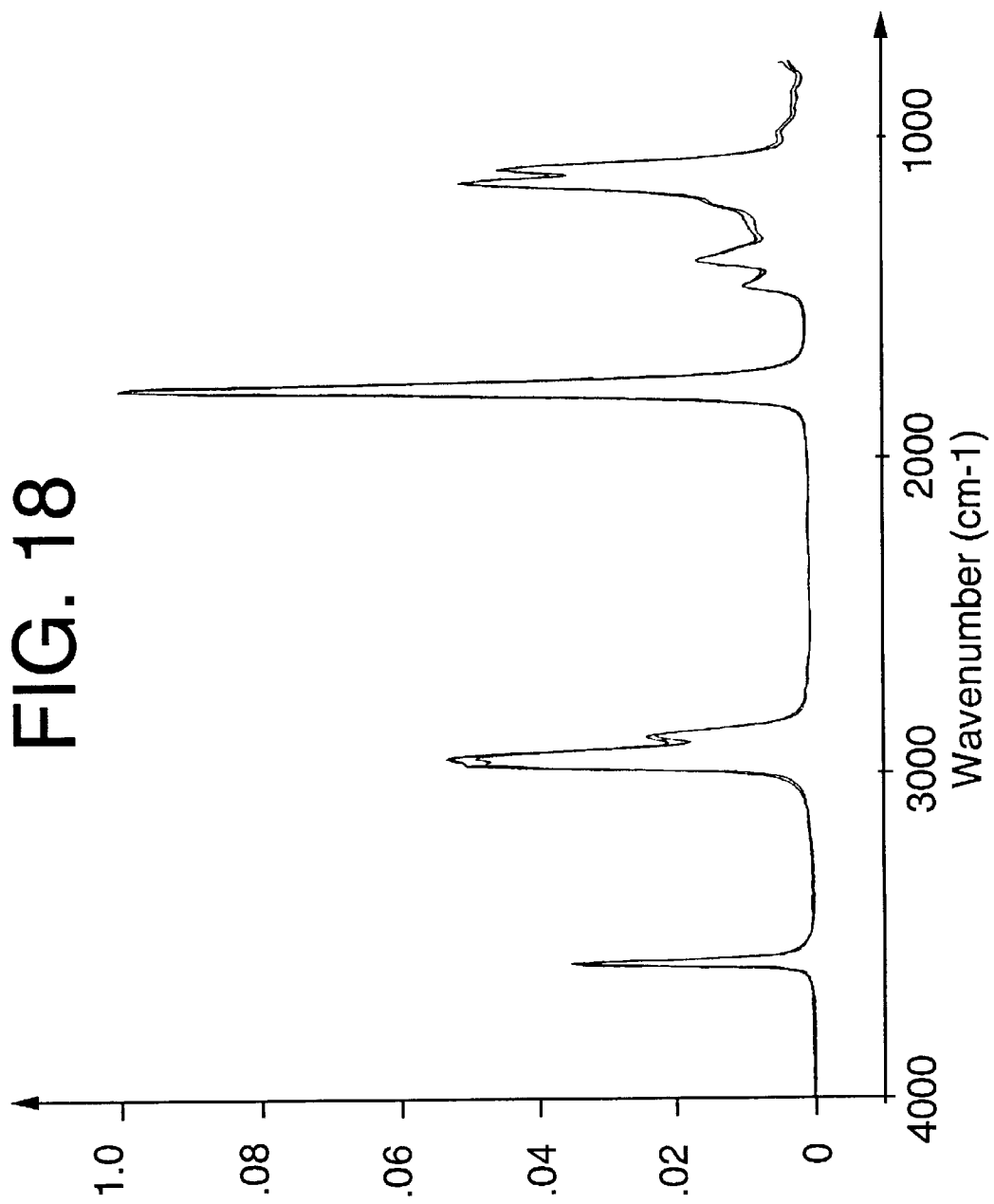

PROCESS FOR PREPARING GAMM-HEXALACTONE, PRODUCTS PRODUCED THEREFROM DAN ORGANOLEPTIC USES OF SAID PRODUCTS

INTRODUCTION AND BACKGROUND

The present invention relates to a two phase microbial process for the preparation of compositions containing γ-hexalactone and, optionally also 2-pentanone. In a further aspect, the present invention relates to products produced by the microbial process.

In a still further aspect, the present invention relates to organoleptic uses of said products.

γ-Hexalactone is also know as γ-caprolactone; ethyl butyrolactone; γ-ethyl-n-butyrolactone; hexanolide-1,4; 4-hydroxy hexanoic acid γ-lactone or tonkalide.

It is characterized by a warm, herbaceous, sweet tobacco-like, coumarinic odor and a sweet, powerful, warm-herbaceous, coumarin-caramel taste. Widely used in perfume composition and for flavoring purposes, it is an important material in the flavor and fragrance industry (Arctander, *Perfume and Flavor Chemicals II*, 1969).

In today's market, it is frequently desirable to identify flavor components of food items as being "natural flavors." It is generally recognized in the industry that a flavor compound having been prepared by microbial processes can be designated as a natural product and therefore have an important place in the commercialization of products containing them. As a result, the industry has devoted considerable time and effort to develop methods for the production of flavoring components and, in particular, for the production of lactones which can be called "natural."

Thus, as an example of such prior developments, a method for preparing certain optically active δ-lactones and the corresponding hydroxy carbocyclic acids by microbial reduction of ketocarboxylic acids is shown in U.S. Pat. No. 3,076,750.

Investigations reported in the *Journal of Biochemistry*, 54, pages 536–540 (1963) relate to metabolism of ricinoleic acid by some Candida strains and show that γ-hydroxydecanoic acid is an intermediate in the oxidative degradation of ricinoleic acid. In a number of such prior disclosed methods, the processes were not entirely satisfactory because of the toxicity of certain components to the microorganism.

A method of producing optically active γ-hydroxydecanoic acid by culturing or incubating a microorganism capable of hydrolyzing castor oil and effecting β-oxidation of the resulting hydrolysate in the presence of castor oil to produce γ-hydroxydecanoic acid is shown in U.S. Pat. No. 4,560,656.

This prior document also discloses a method of producing optically active γ-hydroxydecanoic acid by enzymatically hydrolyzing castor oil using lipase to form an enzymatic hydrolyzate and culturing a microorganism capable of effective β-oxidation of the enzymatic hydrolyzate in the presence of the hydrolyzate to produce γ-hydroxydecanoic acid. Similarly, a way of culturing or incubating the microorganism capable of hydrolyzing castor oil and a microorganism capable of affecting β-oxidation of the castor oil hydrolyzate in the presence of the castor oil to produce γ-hydroxydecanoic acid is also shown in that document.

European Published Patent Application 258993 of Apr. 9, 1988 discloses a process for the production of optically active γ-hydroxydecanoic acid suitable for conversion to optically active γ-decalactone.

Microbial production of natural δ-dodecalactone from Massoi bark oil was discussed by van der Shaft et al. in *Applied Microbiology and Biotechnology* (1992) Vol. 36, pages 712–716.

The usefulness of yeast for reduction reactions in general, including conversion of Massoi lactone is referred to by N. J. Turner in *Chemistry & Industry*, Aug. 1, 1994, pages 592, et seq.

Japanese Application 09 031071-A discloses production of (R)-(-)-massoi lactone by incubating a microorganism.

More recently, in U.S. Pat. No. 5,128,261, 5-decanolide and 5-dodecanolide have been shown to be produced from a series of strains of yeast in a fermentation reaction by carrying out a biocatalytic reduction of the corresponding natural unsaturated 5-olides.

The production of γ-lactone flavor additives using the genus Pityrosporum is shown in Labows et al. U.S. Pat. No. 4,396,715.

The genus Amastigomycota is shown to produce methyl ketones by aerobic biotransformation of $C_6$–$C_{11}$ fatty acids in Creuly, et al., U.S. Pat. No. 4,957,862.

Another process for producing γ-lacotones and δ-lacotones is shown in Page et al., U.S. Pat. No. 5,032,513. The fungus of the genus Mucor is used for this purpose.

Such prior methods are said to be economically attractive but there is a constant need for improvement of yields and conversion which is addressed in this invention.

In the flavor and fragrance art the need has risen for the development of more efficient production of naturally occurring lactones which have heretofore been found to be useful and necessary in the creation of flavor formulation used in augmenting or enhancing the aroma or taste of such items as foodstuffs, chewing gums and toothpastes, and also useful in augmenting or enhancing the aroma of perfume compositions such as colognes, perfumed articles either in solid or liquid state as, for example, ionic, cationic, nonionic or zwitterionic detergents, perfumed polymers, fabric softener compositions, fabric softener articles, hair preparations, cosmetic powders and the like.

It is therefore an object of the present invention to provide a new and improved method for preparing γ-hexalactone which has been found to be suitable for a wide variety of purposes in a more efficient manner to produce a higher yield and greater conversion.

Another object of the present invention is to provide a process for the formation of a plurality of flavor compounds.

SUMMARY OF THE INVENTION

The above and other objects and features of the invention are obtained in accordance in the present invention by carrying out a process using oxidative reaction techniques to produce and recover a naturally occurring saturated lactone; namely, γ-hexalactone found to be useful for its organoleptic properties. A further feature of the present invention resides in a process that will produce 2-pentanone (methyl propyl ketone) and γ-hexalactone at the same time.

Both 2-pentanone and γ-hexalactone are important natural flavor ingredients and are useful in augmenting or enhancing the aroma or taste of consumable materials such as foodstuffs, chewing gums, toothpaste, additional products, chewing tobaccos, smoking tobaccos, perfume compositions, colognes and perfumed articles such as solid or liquid detergents, perfumed polymers, fabric softener compositions, fabric softener articles, cosmetic powders, hair preparations and the like. γ-hexalactone is defined according to the structure:

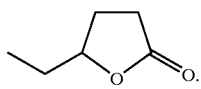

2-Pentanone is represented by the structural formula:

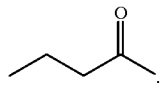

The oxidative reactions to produce the γ-hexalactone and 2-pentanone compositions of the invention are carried out by preparing an aqueous nutrient medium in a first liquid phase, and a second liquid phase which is the organic phase containing a substrate which is the hexanoic acid starting compound represented by the structural formula:

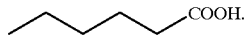

The first aqueous liquid phase and the second liquid phase are mixed together in the presence of a fungus with agitation to form an incubation system while aerating with an oxygen containing gas such as air or oxygen in a sufficient amount to maintain oxidative conditions in the incubation system to thereby achieve an oxidation reaction and conversion of hexanoic acid into the desired products.

The reaction can be schematically represented as follows:

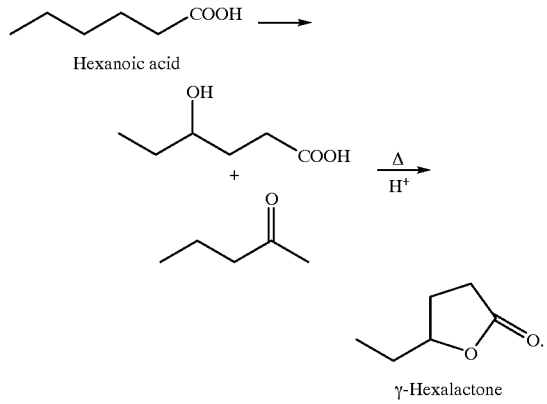

A further feature of the present invention resides in the products produced by the present invention characterized by the GLC profiles which accompany this application.

Still further, another feature of the invention resides in the flavor and fragrance compositions containing the products produced by the present invention.

BRIEF DESCRIPTION OF THE DRAWINGS

The present invention will be further understood with reference to the accompanying drawings wherein.

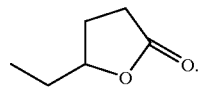

Figure 1:
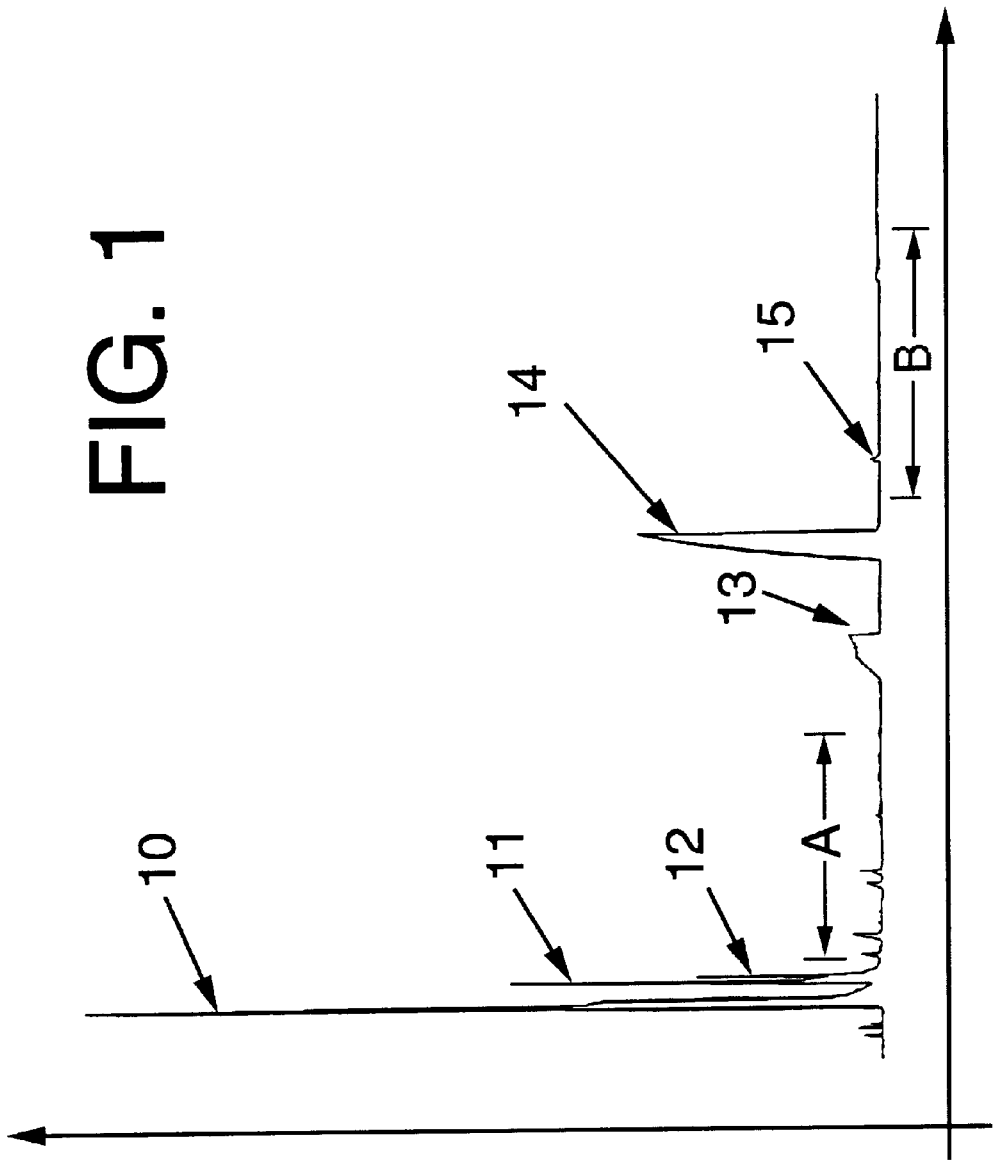
FIG. 1 is a total ion chromatogram (TIC) of the reaction product for Example 1 containing the compound having the structure.
Figure 2:
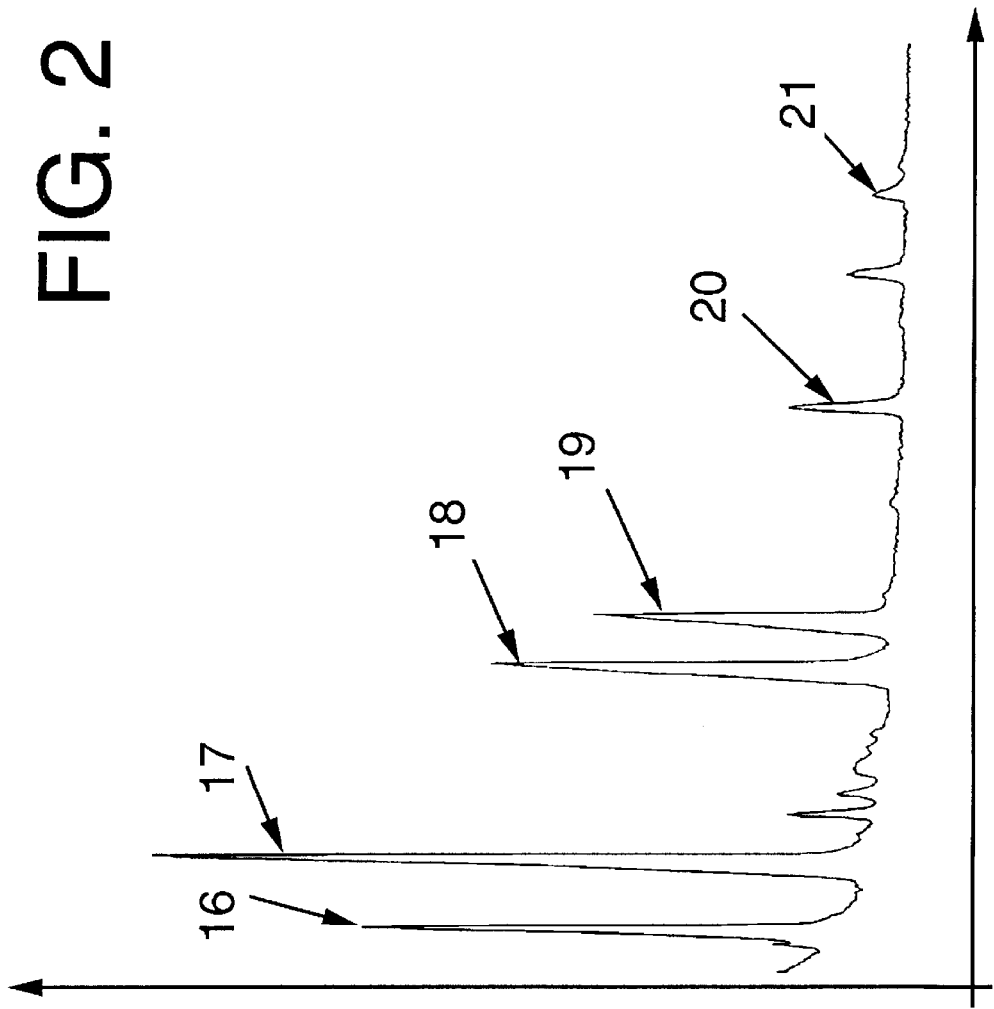

FIG. 2 is an enlarged section of the TIC of FIG. 1 identified by the marker "A" for the reaction product of Example 1 containing the compound having the structure:

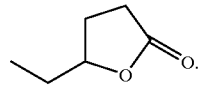

Figure 3:
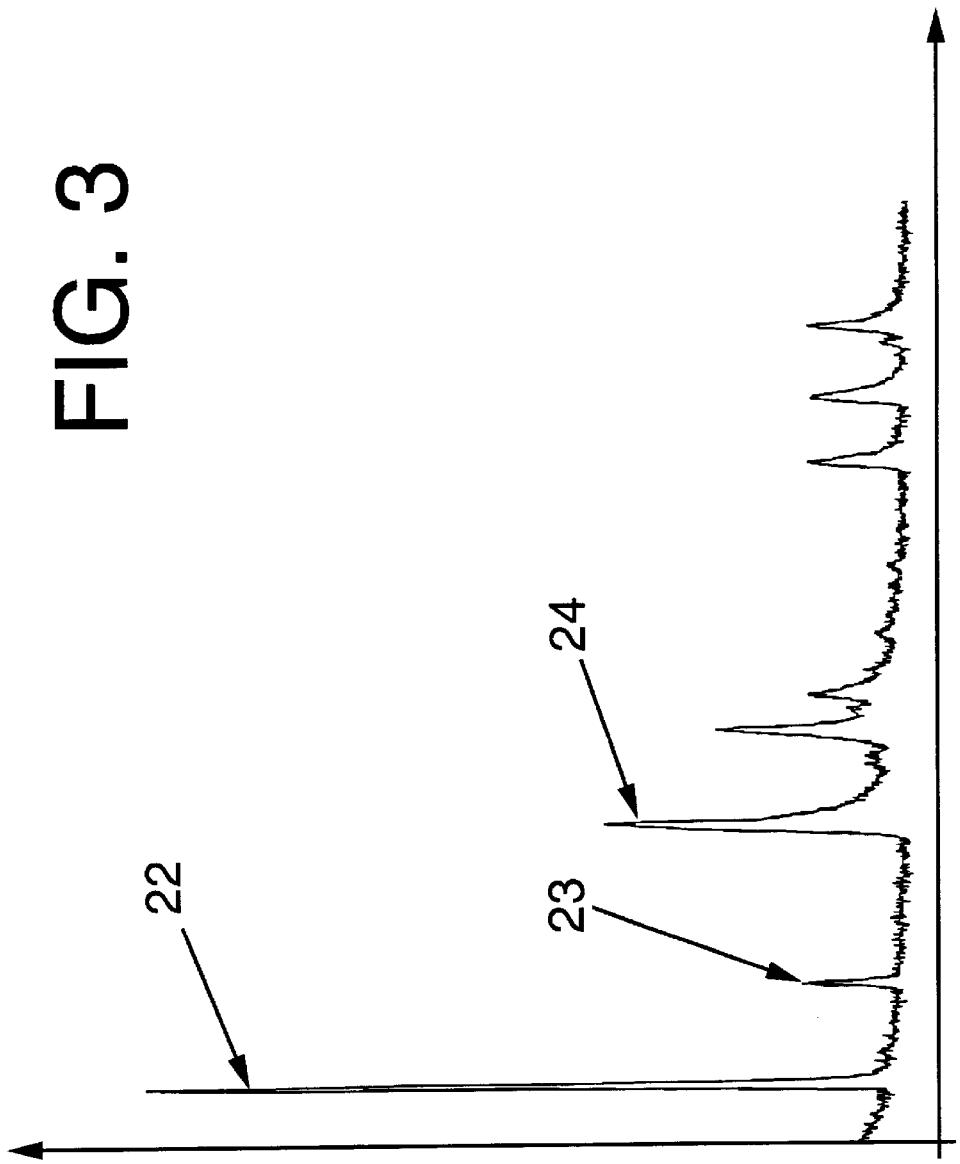

FIG. 3 is an enlarged section of the TIC of FIG. 1 identified by the marker "B" for the reaction product of Example 1 containing the compound having the structure:

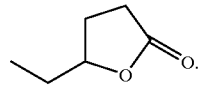

Figure 4:
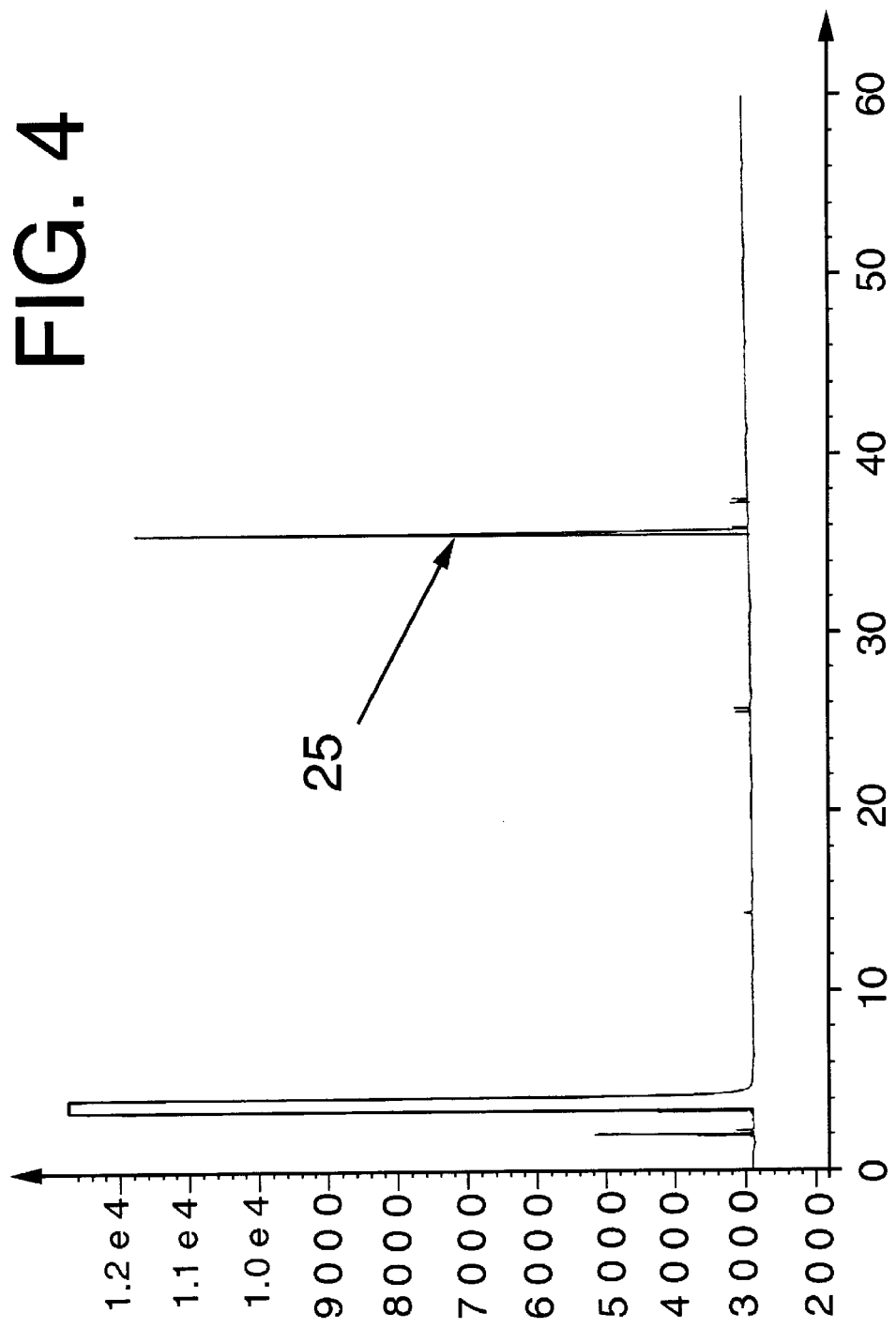

FIG. 4 is a GC/chiral column profile of the reaction product of Example 1 containing the compound having the structure:

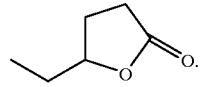

Figure 5:
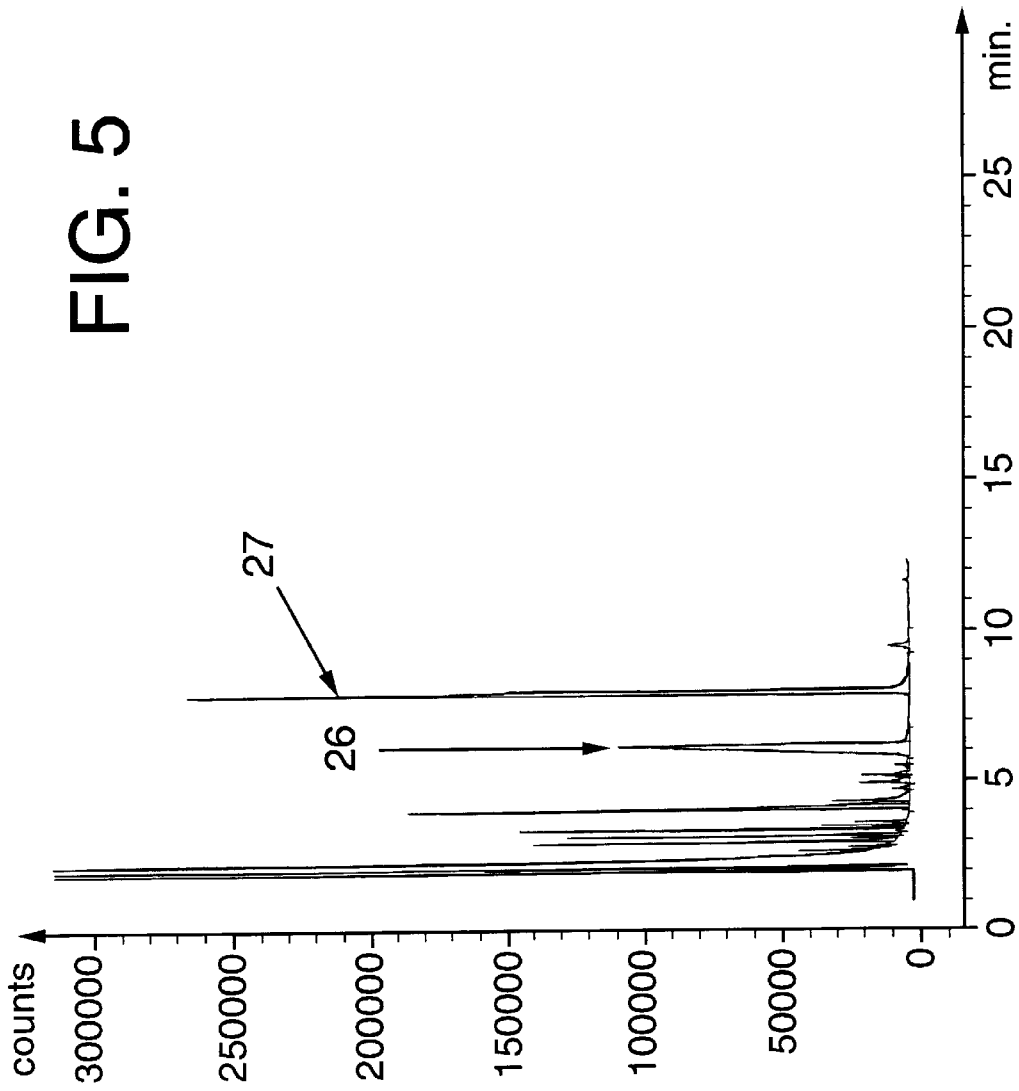

FIG. 5 is a GC profile for the reaction product of Example 19 containing the compound having the structure:

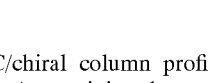

Figure 6:
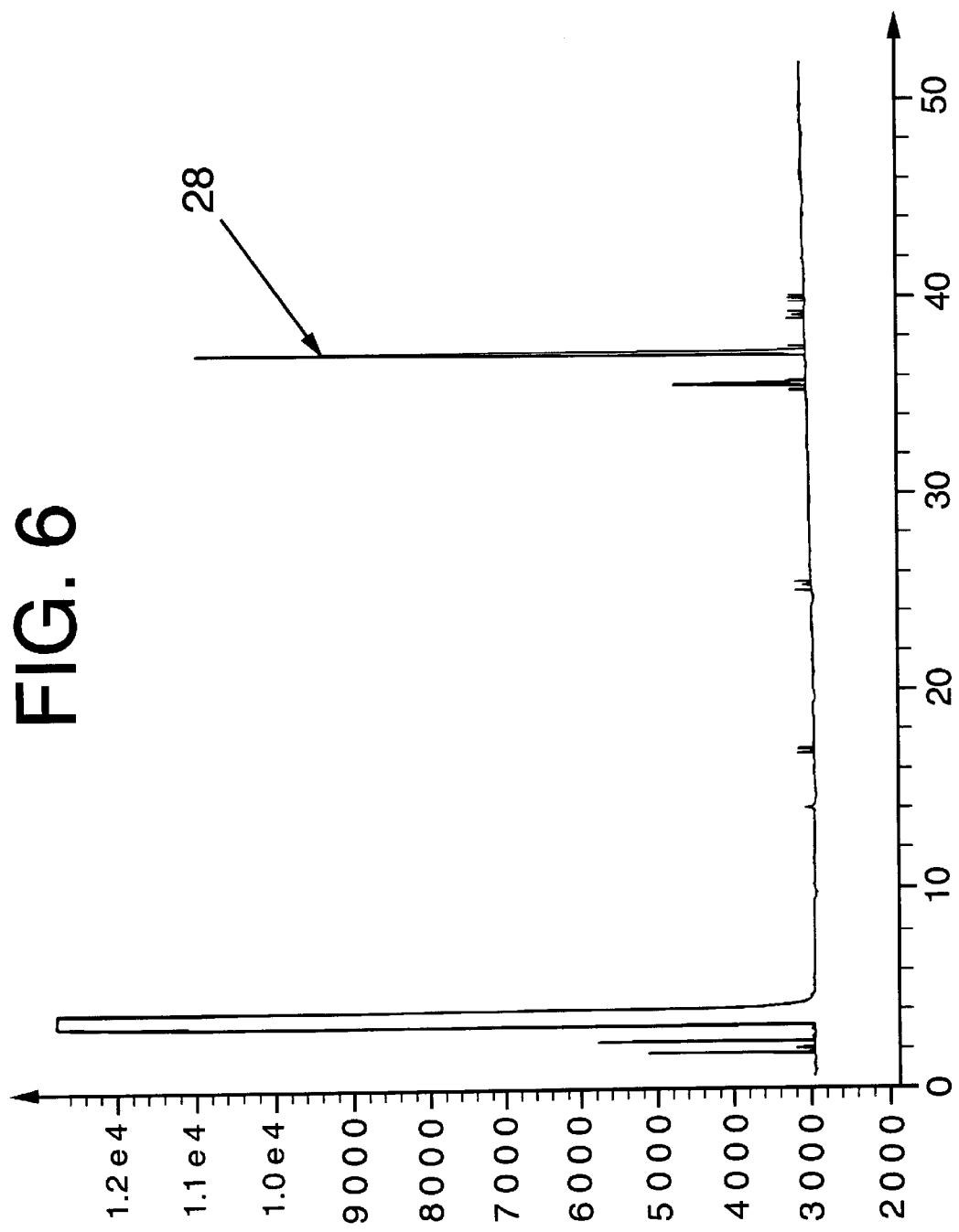

FIG. 6 is a GC profile for the reaction product of Example 20 containing the compound having the structure:

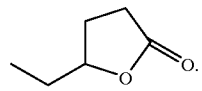

Figure 7:
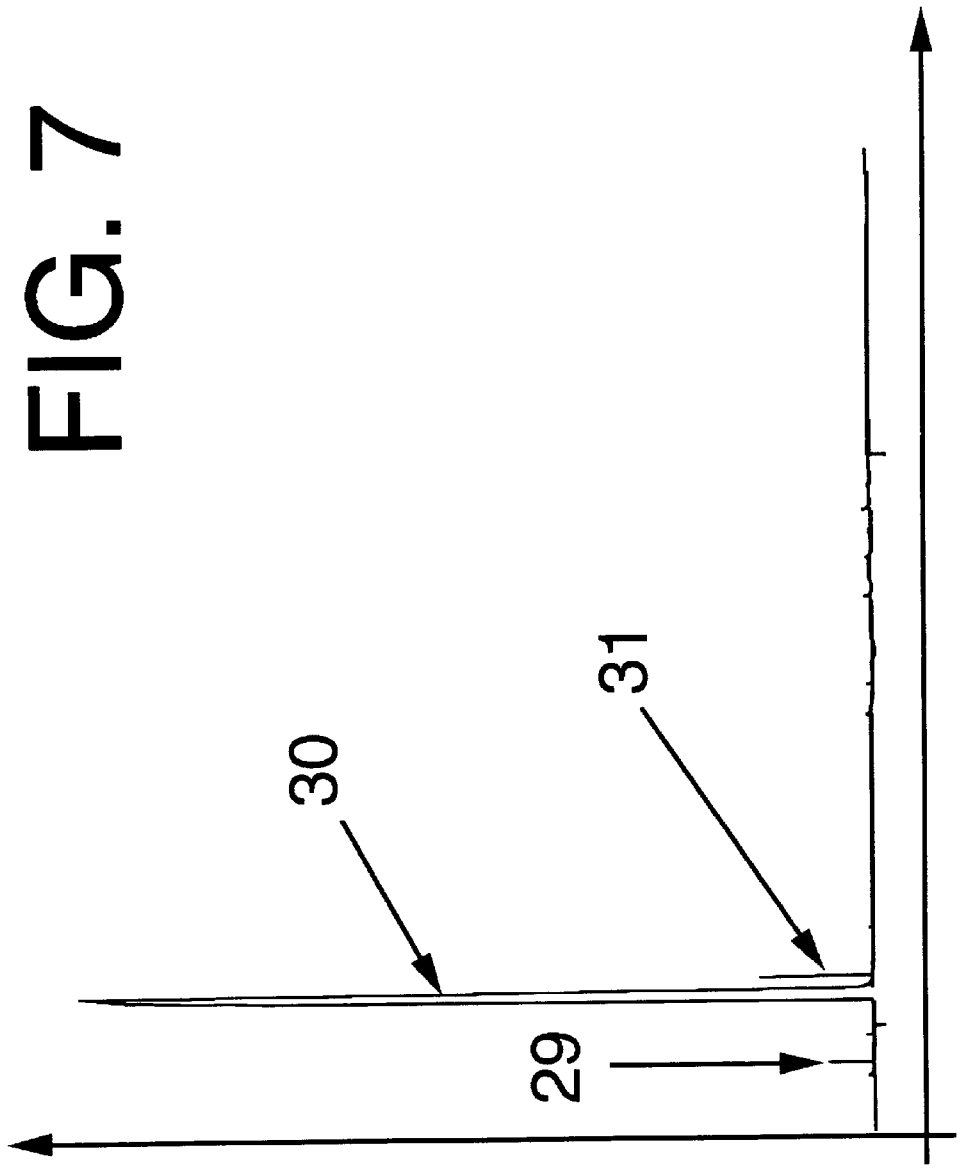

FIG. 7 is a an MS-GC profile for the reaction product of Example 21 containing the compound having the structure:

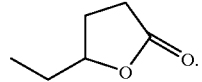

Figure 8:
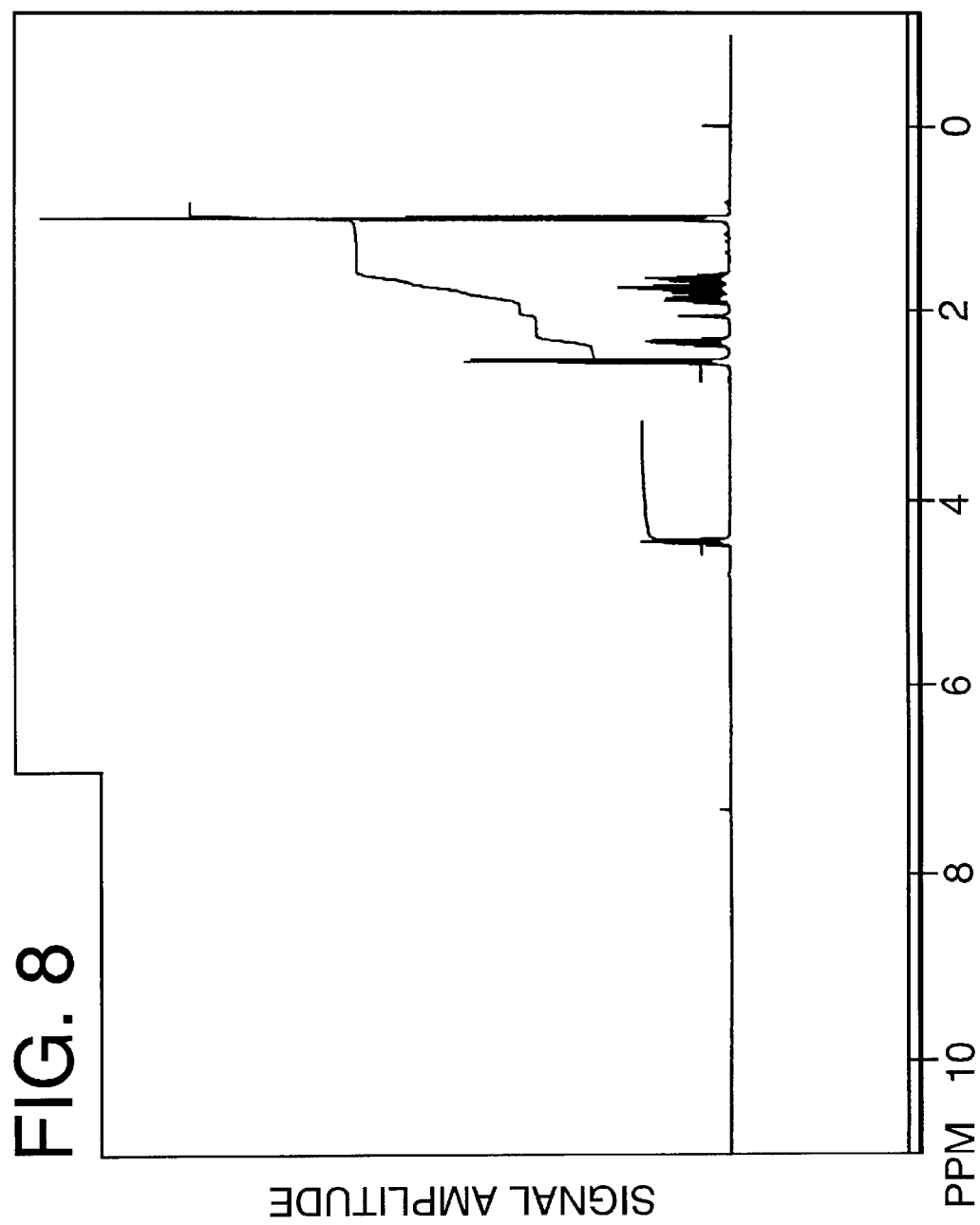

FIG. 8 is an NMR analysis for the γ-lactone for Example 21.

Figure 9:
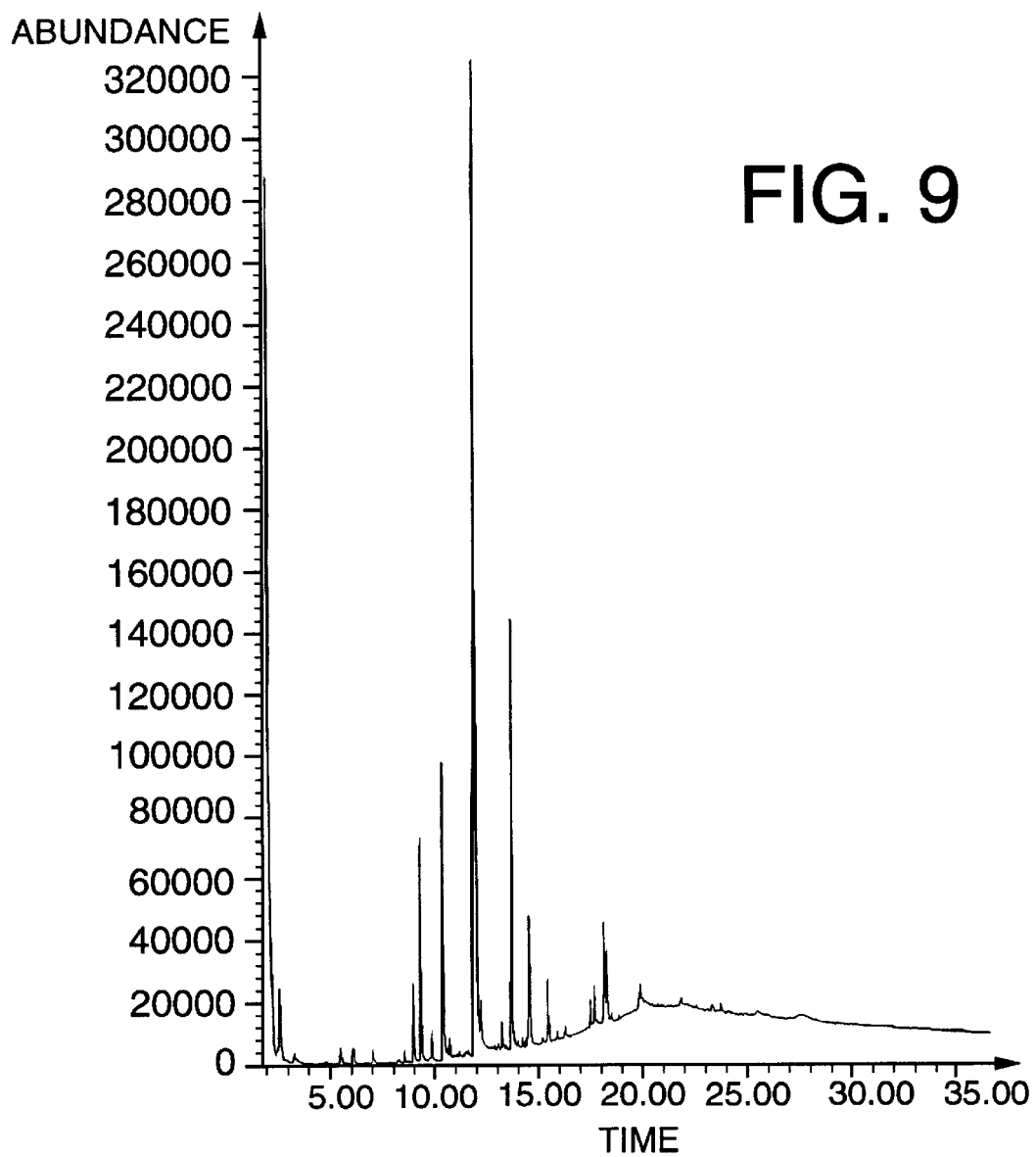

FIG. 9 is a TIC of γ-hexalactone extract for Example 22.

Figure 10:
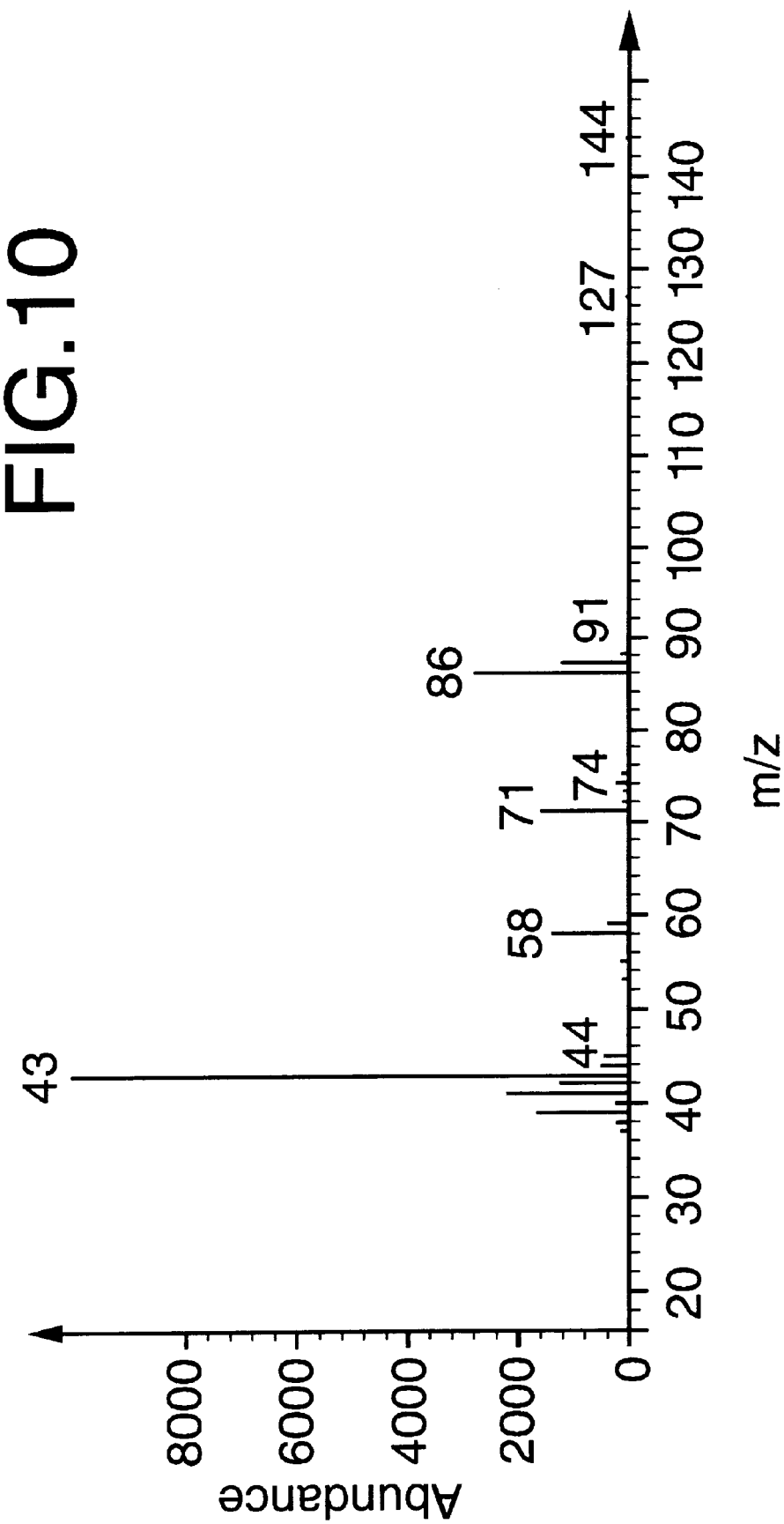

FIG. 10 is a mass spectrum of 2-pentanone in sample and the standard spectrum for Example 22.

Figure 11:
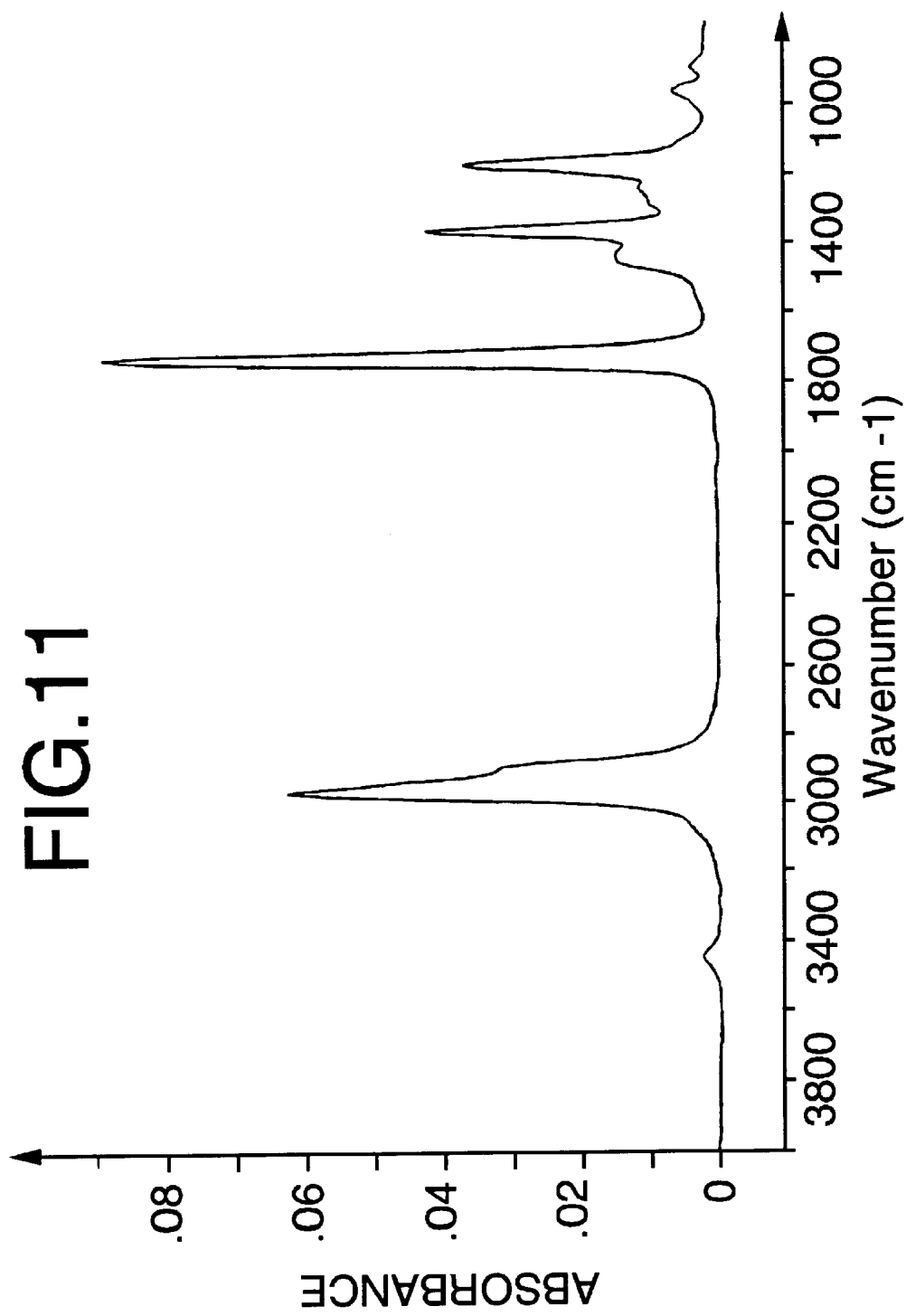

FIG. 11 is a gas-phase infra-red spectrum of 2-pentanone in the graph for Example 22.

Figure 12:
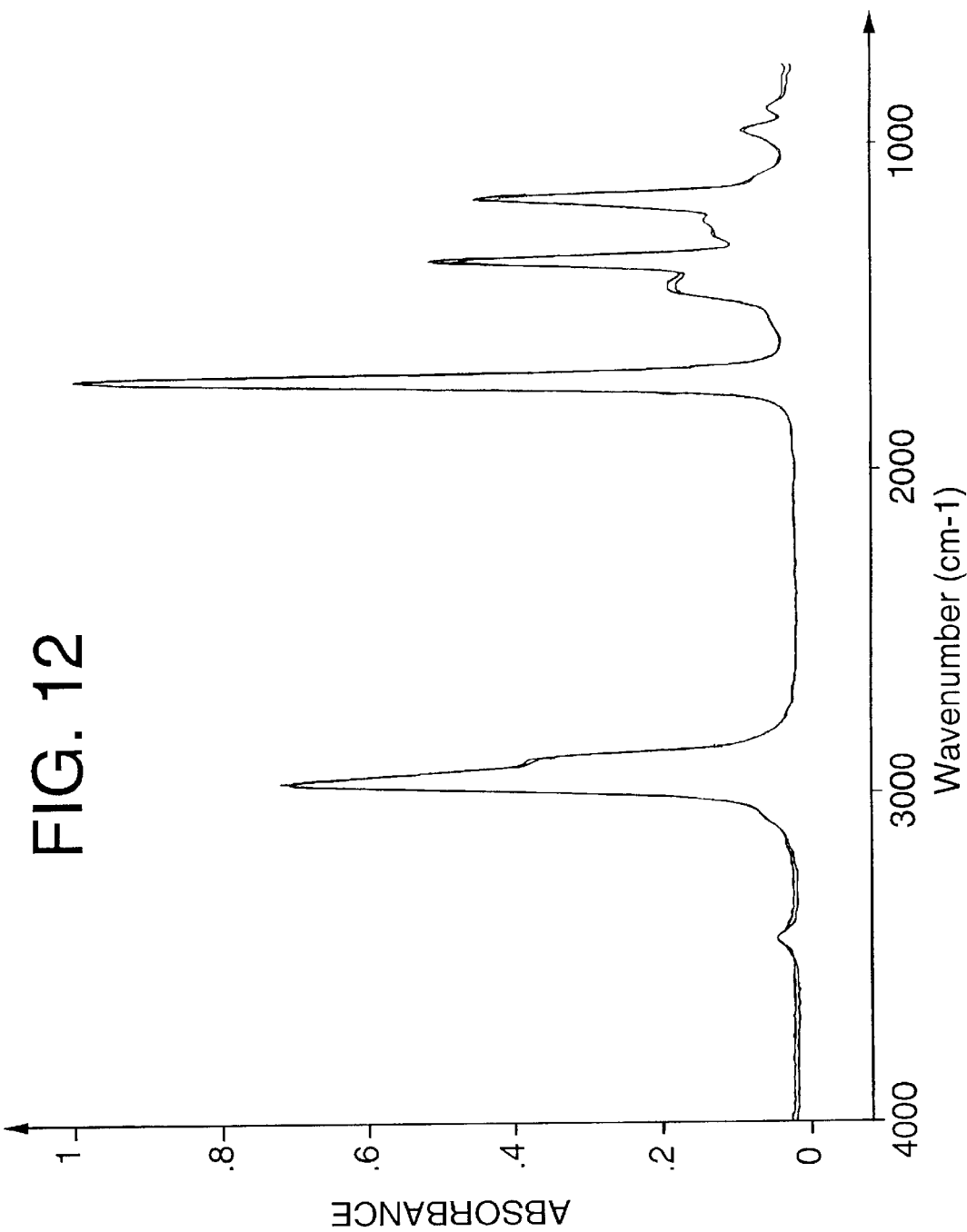

FIG. 12 is a gas phase infra red spectrum of 2-pentanone in sample overlayed with the standard 2-pentanone spectrum for Example 22.

Figure 13:
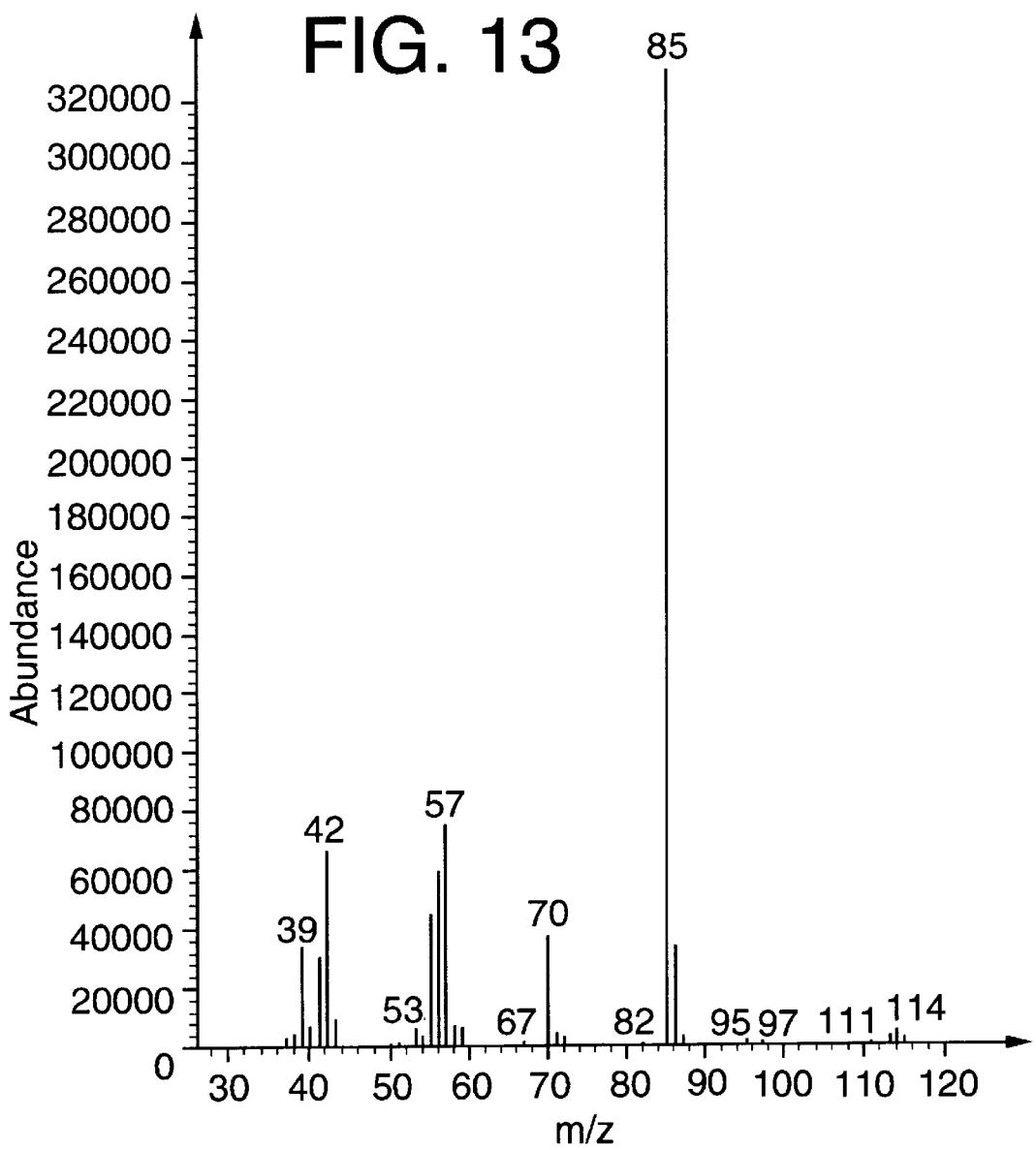

FIG. 13 is a mass spectrum (electron impact ionization) of γ-hexalactone in sample and the standard spectrum for Example 22.

Figure 14:
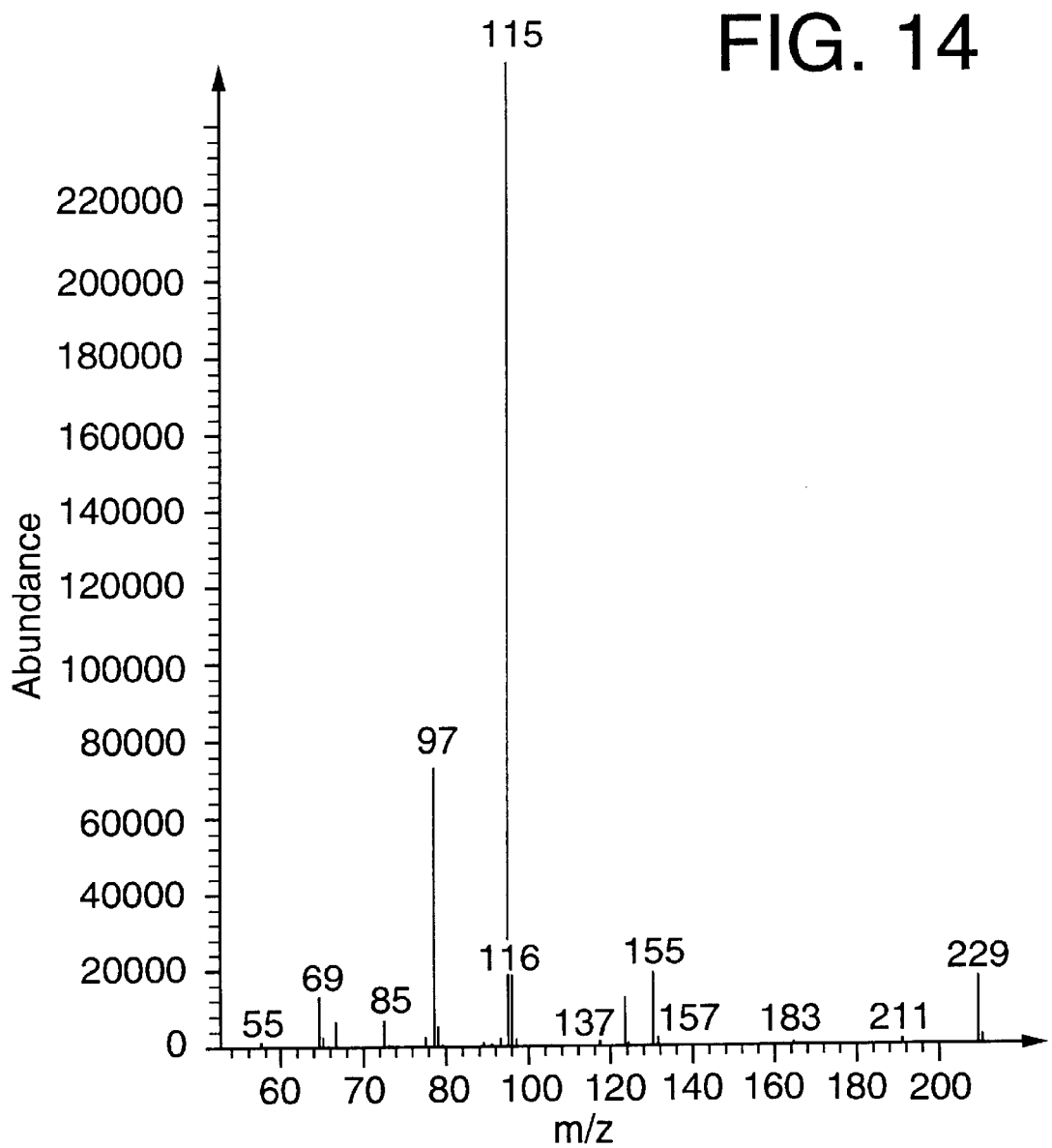

FIG. 14 is a mass spectrum (chemical ionization) of γ-hexalactone in the sample of Example 22.

Figure 15:
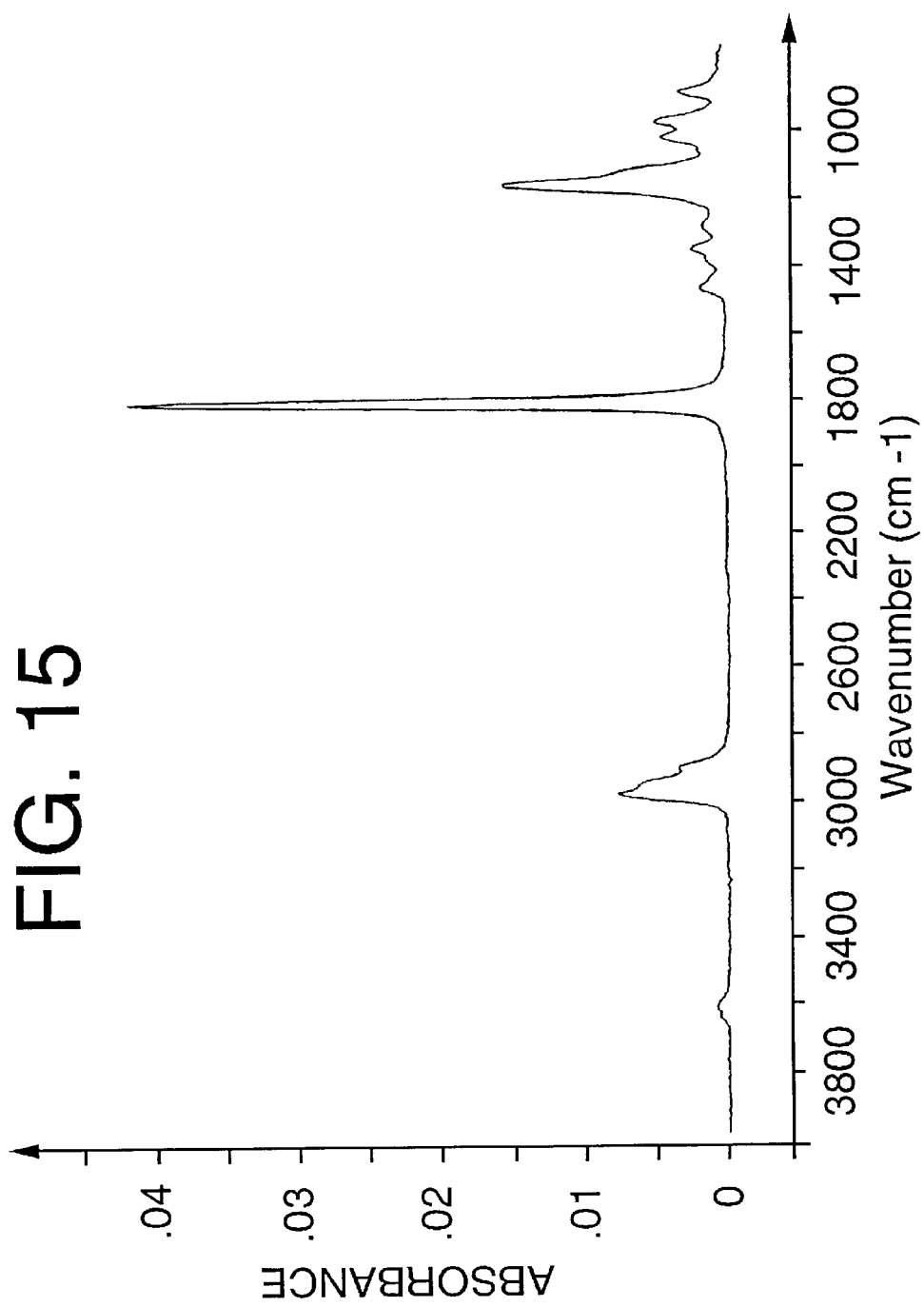

FIG. 15 is a gas phase infra-red spectrum of γ-hexalactone of Example 22.

Figure 16:
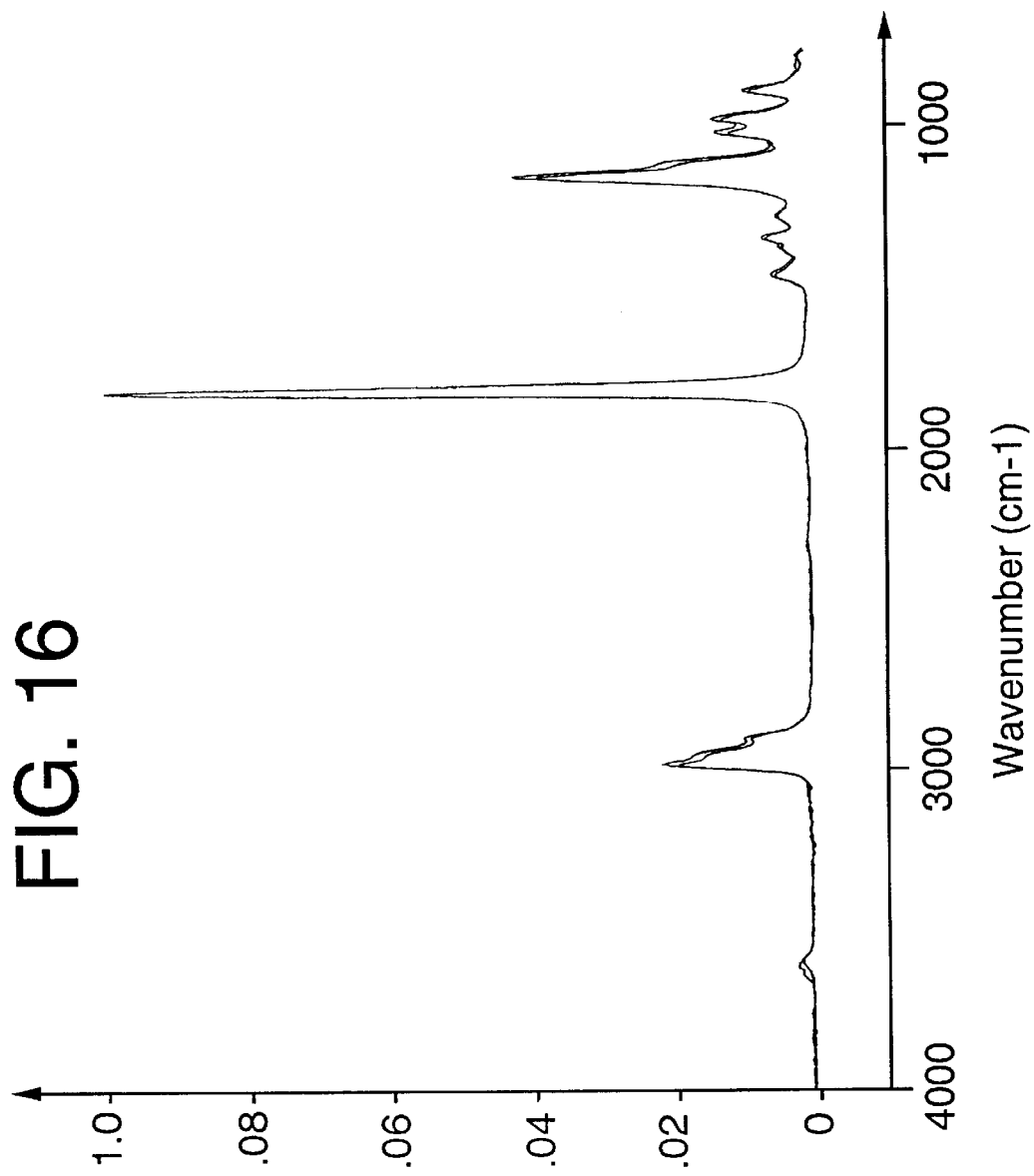

FIG. 16 is a gas phase infra-red spectrum of γ-hexalactone in Example 22 overlayed with the standard γ-hexalactone spectrum.

FIG. 17 is a mass spectrum (electron impact ionization) of hexanoic acid in Example 22 and the standard spectrum.

FIG. 18 is a gas phase infra-red spectrum of hexanoic acid in Example 22 overlayed with the standard hexanoic acid spectrum.

DETAILED DESCRIPTION OF INVENTION

The reaction according to the present invention is shown thusly:

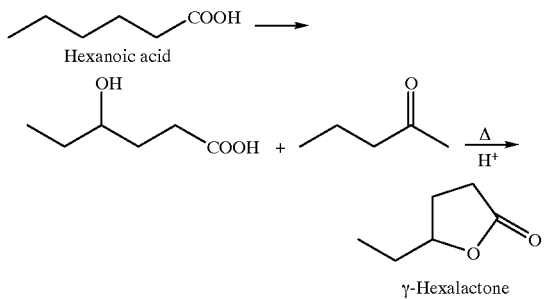

More specifically, the oxidative reaction involves the use of an oxygen containing gas such as air or oxygen which is dissolved in a relatively high amount into the reaction medium. In the process of the invention the mold fungus is used, preferably the Aspergillus or Mortierella variety. A number of such molds can be used to obtain comparable results.

The process is carried out by first introducing an inoculum of the selected fungus species into a reaction vessel which contains a production medium, typically including a nutrient source, a buffering agent such as sodium phosphate alkali and/or alkaline earth salts, trace minerals, vitamins and the like. The production medium is the first liquid phase and is an aqueous phase. A source of sugar can be used in a suitable nutrient medium for feeding into the reaction vessel.

Following inoculation with the fungus species, and with commencement of feeding of the nutrient medium, a mixture of the γ-hexanoic acid and a suitable diluent as an optional component as the substrate is pumped into the reaction vessel. A particularly suitable diluent is PRIMOL® or water.

The nutrient feed which may contain the source of sugar and may also contain a solution of vitamins as desired and trace mineral solutions as desired as well as buffers, and the like is pumped into the reaction vessel.

It is to be understood that the production medium and the nutrient medium suitable for the present invention are well known and understood by persons skilled in this art.

The oxidative reaction is permitted to proceed being careful to maintain oxidation conditions in the reaction vessel by balancing the nutrient feed and oxygen injection into the system. The concentration of the sugar, which is preferred as the nutrient, is maintained at least about 5 grams per liter to as much as 25 grams per liter, preferably, most preferably at about 15 grams per liter during the oxidative fermentation. The actual concentration varies at any given time from a minimum to a maximum recognizing that too much sugar will result in production of $CO_2$ instead of the desired product. By automatic addition of the nutrient feed, the nutrient feed rate can range from about 5 grams up to about 20 grams per hour per liter. Dextrose is the preferred source of sugar.

The desired temperature of the reaction is approximately 30° C. although this can vary as will be understood by persons skilled in this art. The optimum temperature of the reaction can be readily determined by skilled operators using parameters well understood in the fermentation art. A typical range of temperature is 20 to 50° C. It is a feature of the oxidation fermentation reaction of the present invention to avoid the formation of excessive amounts of undesired compounds. Under the reaction conditions discovered by applicants, unwatered compound production is avoided by an inventive control of the sugar addition and charging of the oxygen source to the system. Thus, the rate of sugar addition and oxygen source addition is such as to maintain oxidation conditions in the reaction medium and enabling the substrate; namely, the hexanoic acid compound to slowly diffuse into the first phase and thereby control the reaction to form the desired compounds and avoid the formation of unwanted substances.

As an example of oxygen in the system, the oxygen is produced at a rate which is at least about 0.1 liters per liter per minute of reaction mixture and may be as high as 2 liters per liter per minute. The injection of air or other oxygen containing gas is controlled so as to measure at least 100% dissolved oxygen as measured by a standard oxygen probe at all times during the reaction. Typical dissolved oxygen readings during the reaction are 0–100% (e.g., "50%" or "60%"). In the fermentation batch, the concentration of dissolved oxygen varies between 1 and 10 mg/liter and is a function of the temperature existent in the batch at a particular instant in time as well as the pressure above the batch (usually atmospheric pressure, but may be as high as 5 atmospheres pressure).

The resulting products in the form of γ-hexalactone and 2-pentanone are useful in augmenting or enhancing the aroma or taste of consumable materials as set forth herein.

According to a second embodiment of the invention, by employing appropriate collection means, it is possible to recover the normally volatilized 2-pentanone.

The form in which the fungus microorganism is used is not critical. It can be used as a culture in a suspension including the cells and the corresponding nutrient solution or in the form of cells suspended in a buffering solution. The cells or an enzyme extract thereof may be immobile on a suitable solid support which may then be used to effect the transformation.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinose, L-rhamnose, ethanol, glycerol, L-erythritol, D-mannitol, lactose, melibiose, raffinose, melezitose, starch, D-xylose, D-sorbitol, α-methyl-D-glucoside, lactic acid, citric acid and succinic acid. Among the suitable nitrogen sources are, for example, nitrogen containing organic substances such as peptone, meat extract, yeast extract, corn steep liquor, casein, urea, amino acids, or nitrogen containing inorganic compounds such as nitrates, nitrites, and inorganic ammonium salts. Among the suitable inorganic salts are, for example, phosphates of magnesium, potassium, calcium and sodium. The above mentioned nutrients in the culture medium may be supplemented with, for example, one or more vitamins of the B Group and/or one or more trace minerals such as Fe, Mo, Cu, Mn, B as desired. However, the process can be performed in a vitamin-free medium.

The cultivation of the microorganism can be carried out as a stationary culture or as a submerged culture (e.g. shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as aqueous or gaseous ammonia, sodium hydroxide, potassium hydroxide, calcium hydroxide, calcium carbonate, by ion-exchange resins, or by the addition of a buffer such as a phosphate or a phthalate. The incubation temperature is suitably maintained at between about 15° C. and about 33° C., with a range from about 20° C. to about 30° C. being preferred.

Examples of suitable microorganisms are:

*Aspergillus oryzae* NRRL 2217;

*Aspergillus oryzae* NRRL 2220;

*Aspergillus oryzae* NRRL 1989;

*Aspergillus oryzae* NRRL 3485;

*Aspergillus oryzae* NRRL 3488;

*Aspergillus parasiticus* NRRL 1731;

*Aspergillus oryzae* NRRL 695;

Aspergilius sp. IFF-8188 (ATCC 74479); and

*Mortierella isabellina* 7873 (CBS 221.29).

The process in accordance with the invention is conveniently carried out by adding a source of sugar, such as dextrose to the culture medium at the onset of cultivation, as the carbon source. Alternatively, the dextrose may be added in combination with another carbon source, as mentioned above, either during cultivation, or when the cultivation is complete. The amount level, or concentration of the substrate in the medium may vary. For example, in the case of sources of sugar, levels of from about 0.26 to about 9.0% may make up the medium initially or be added during the course of the oxidation reduction, although the specific level of sugar source may be easily determined and can be varied.

The reaction time may vary depending on the composition of the culture medium and the substrate concentration. In general, shaking flask cultures require from between about 2 h. and about 240 h. depending upon the microorganism and the composition of the culture medium. However, when a fermenter vessel is used the oxidative reduction reaction time may be reduced to about 100 h. or less.

The reaction of this invention may be carried out using the cells of the microorganism isolated from the culture solution, or with an enzyme extract isolated from the cells in a manner known per se. In this case, the reaction can be conveniently carried out in aqueous solution, for example, in a buffer solution, in a physiological salt solution, in a fresh nutrient solution, or in water. The isolated cells or enzyme extract may be immobilized on a solid support and the desired transformation effected in the absence of the live microorganism. The transformation of the substrate may be effected by mutants of the microorganism. Such mutants can be obtained readily by methods well known in the art, for example, by exposing the fungus to UV or X-rays, or customary mutagenic substances such as, for example, acridine orange.

The substrate which is the hexanoic acid compound is generally added directly to the production medium. Sources for the hexanoic acid can vary but any commercial source would be suitable. It is to be understood that a salt, alkyl ester, mono, di or triglyceride, or amide of the hexanoic acid can also be used as a suitable substrate. Hence, the term "hexanoic acid" as used herein is intended to encompass the above.

Conventional antifoam agents, such as silicone oils (e.g., UCON®), polyalkyleneglycol derivatives, maize oil, or soya oil can be used to control foaming as is known in the art.

The γ-hexalactone can be recovered by conventional systems. The volatile 2-pentanone can be trapped in a carbon trap or recovered in other conventional ways.

The γ-hexalactone and the 2-pentanone compounds obtained in accordance with the present invention can be used separately with one or more auxiliary perfume ingredients, including for example, hydrocarbons, alcohols, ketones, aldehydes, nitriles, esters, ethers, synthetic essential oils, and natural essential oils or may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, the compounds produced in accordance with the described process can be used to alter, modify or enhance the aroma characteristics of a perfume composition, for example, by utilizing or moderating the olfactory reaction contributed by another ingredient in the composition.

The amount of the compounds described herein which will be effective in perfume compositions as well as in perfumed articles and colognes depends upon many factors including the other ingredients, their amounts and the effects which are desired. It has been found that perfume compositions containing as little as 0.005% of the compounds described herein or even less (e.g., 0.0025%) can be used to impart sweet, fruity aromas to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The compounds described herein are useful when either taken alone or taken together with other perfumery ingredients in detergents, soaps, space odorants and deodorants, perfumes, colognes, toilette waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the compounds described herein can suffice to impart intense, substantive, sweet, fruity aroma to floral perfume formulations. Generally no more than 5% of the compound based on the ultimate end product is required to be used in the perfume compositions.

Furthermore, as little as 0.255% of the compound can suffice to impart such aromas to perfumed articles per se, whether in the presence of other perfume materials or whether used by themselves. Thus, the range of use of the compounds described herein in perfumed articles, e.g., perfumed polymers and solid or liquid anionic, cationic, non-ionic or zwitterionic solid or liquid detergents, may vary from 0.25% up to about 5% by weight based on the total weight of the perfumed article.

In addition, the perfume composition or fragrance compositions to be described below can contain a vehicle or carrier for the γ-hexalactone and/or 2-pentanone compounds. The vehicle can be a liquid such as a non-toxic alcohol, e.g., ethanol, a non-toxic glycol, e.g., propylene glycol, or the like. The carrier can also be an absorbent solid such as a gum (e.g, gum arabic or xanthan gum or guar gum) or components for encapsulating the composition by means of coacervation (such as by gelatin) or by means of formulation of a polymer around a liquid center. This can be accomplished by using a urea formaldehyde prepolymer to form a polymeric capsule around a perfume composition center as is known in the art.

It will be appreciated from the present disclosure that the γ-hexalactone and 2-pentanone compounds according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplement the existing flavor impression to modify its organoleptic character.

The term "enhance" is intended herein to mean the intensification (by use of the compound of this invention) of a flavor or aroma note or nuance in a foodstuff or perfume composition or perfumed article without changing the quality of said note or nuance.

A "flavoring composition" as referred to herein means one which contributes a part of the overall flavor impression by supplementing or fortifying a natural or artificial flavor in a material or one which supplies substantially all the flavor and/or aroma character to a consumable article.

The term "foodstuff" as used herein included both solid and liquid ingestible material for man or animals which materials usually do, but need not, have nutritional value. Thus, foodstuffs include meats, gravies, soups, convenience foods, malt, alcoholic and other beverages, milk and diary products, seafood, including fish, crustaceans, mollusks and the like, candies, vegetables, cereals, soft drinks, snacks, dog and cat foods, other veterinary products, and the like.

When the compounds of this invention are used in a flavoring composition, they can be combined with conventional flavoring materials or adjuvants. Such co-ingredients or flavoring adjuvants are well known in the art for such and have been extensively described in the literature. Requirements of such adjuvant materials are: (1) that they be non-reactive with the compound(s) of this invention; (2) that they be organoleptically compatible with the compound(s) of this invention whereby the flavor of the ultimate consumable material to which the compound(s) are added is not detrimentally affected by the use of the adjuvant; (3) that they be ingestible acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids, alcohols including primary and secondary alcohols, esters, carbonyl compounds including ketones and aldehydes; lactones; other cyclic organic materials including benzene derivatives, alicyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil, and the like and artificial flavoring materials such as vanillin and the like.

Specific preferred flavor adjuvants are as follows:

anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil
3,4-dimethoxyphenol;
amyl acetate;
amyl cinnamate;
γ-butyryl lactone;
furfural;
trimethyl pyrazine;
phenyl acetic acid
isovaleraldehyde;
ethyl maltol;
ethyl vanillin;
ethyl valerate;
cocoa extract;
coffee extract;
peppermint oil;
spearmint oil;
clove oil;
anethol;
cardamom oil,
wintergreen oil;
cinnamic aldehyde;
ethyl-2-methyl valerate;
gamma hexenyl lactone;
2,4-decadienal;
2,4-haptadienal; and
butylidene phthalide.

DETAILED DESCRIPTION OF DRAWINGS

The accompanying profiles illustrate products obtained by carrying out the procedures described in the examples and show slightly different peaks which represent differences in yield.

FIG. 1 is a TIC profile for the reaction product of Example 1. The peak indicated by reference numeral 10 is the peak for the compound having the structure:

The peak indicated by reference numeral 11 is the peak for the compound having the structure:

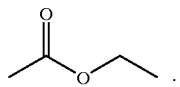

The peak indicated by reference numeral 12 is the peak for the compound having the structure:

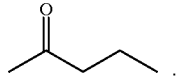

The peak indicated by reference numeral 13 is the peak for the compound having the structure:

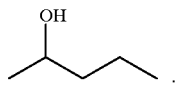

The peak indicated by reference numeral 14 is the peak for the compound having the structure:

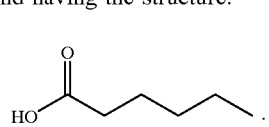

The peak indicated by reference numeral 15 is the peak for the compound having the structure:

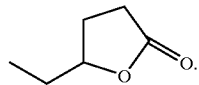

FIG. 2 is a section of the profile from FIG. 1(A) for the reaction product of Example 1. The peak indicated by reference numeral 16 is the peak for the compound having the structure:

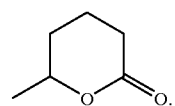

The peak indicated by reference numeral 17 is the peak for the compound having the structure:

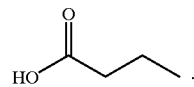

The peak indicated by reference numeral 18 is the peak for the compound having the structure:

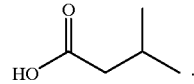

The peak indicated by reference numeral 19 is the peak for the compound having the structure:

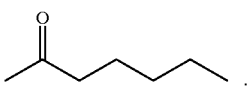

The peak indicated by reference numeral 20 is the peak for the compound having the structure:

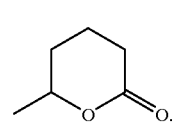

The peak indicated by reference numeral 21 is the peak for the compound having the structure:

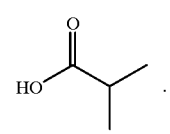

FIG. 3 is a section of the profile in FIG. 1 for the reaction product of Example 1. The peak indicated by reference number 22 is for the compound having the structure:

The peak indicated by the reference number 23 is for the compound having the structure:

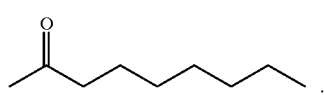

The peak indicated by the reference number 24 is for the compound having the structure:

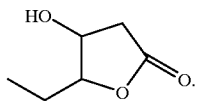

FIG. 4 is a GC/chiral column profile for the reaction product of Example 1. The peak indicated by reference number 25 is for the compound having the structure:

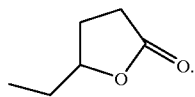

FIG. 5 is a GC profile for the reaction product of Example 19. The peak indicated by the reference number 26 is for the compound having the structure:

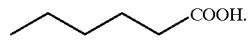

The peak indicated by the reference number 27 is for the compound having the structure:

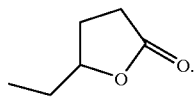

FIG. 6 is the GC profile for the reaction product of Example 20. The peak indicated by the reference number 28 is for the compound having the structure:

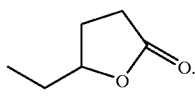

FIG. 7 is the MS-GC profile for the reaction product of Example 21. The peak indicated by the reference numeral 29 is for the compound having the structure:

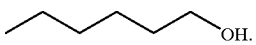

The peak indicated by the reference number 30 is for the compound having the structure:

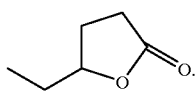

The peak indicated by the reference number 31 is for the compound having the structure:

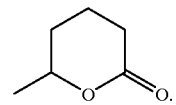

FIG. 8 is the NMR analysis for the γ-hexalactone of Example 21.

FIG. 9 is a total ion chromatogram of γ-hexalactone extract for Example 22.

FIG. 10 is the mass spectrum (electron impact ionization) of 2-pentanone in sample and the standard spectrum for Example 22.

FIG. 11 is the gas phase infra-red spectrum of 2-pentanone in sample for Example 22.

FIG. 12 is a gas phase infra-red spectrum of 2-pentanone in sample overlayed with the standard 2-pentanone spectrum for Example 22.

FIG. 13 is a mass spectrum (electron impact ionization) of gamma-hexalactone in sample and the standard spectrum for Example 22.

FIG. 14 is a mass spectrum (chemical ionization) of gamma-hexalactone in sample, showing the molecular ion (M+1=115) of Example 22. Molecular weight of γ-hexalactone is 114.

FIG. 15 is a gas phase infra-red spectrum of γ-hexalactone (caprolactone) in sample for Example 22.

FIG. 16 is a gas phase infra-red spectrum of γ-hexalactone in sample overlayed with the standard γ-hexalactone spectrum for Example 22.

FIG. 17 is a mass spectrum (electron impact ionization) of hexanoic acid in sample and the standard spectrum for Example 22.

FIG. 18 is a gas phase infra-red spectrum of hexanoic (caproic) acid in sample overlayed with the standard hexanoic acid spectrum for Example 22.

The MS-GC in FIG. 7 was prepared from a methyl silicon column 50 meters in height by 0.32 mm using 0.3 micron bonded fused silica, operated at an initial temperature of 75° C. up to a final temperature of 225° C. at 2° C. per minute for a total time of 30 hours.

The following examples serve to illustrate the present invention.

EXAMPLE 1

The following medium was prepared in a 14 L fermenter:
Medium
10 g/l AMBEREX® 1003;
7.4 g/l Sodium Phosphate, monobasic, $H_2O$;
3.3 g/l Sodium Phosphate, dibasic, $7H_2O$;
283 g/l Primol;
6.0 L deionized water; and
pH adjusted to 6.5 maintained with 25% NaOH.
Inoculum
20 g MISO TANE KOJI® Spores wetted in 100 ml of YM® media for 1 hour at 150 RPM before adding to fermenter.
Fermenter Parameters
Temperature: 30° C.;
Agitation: 800 RPM;
Aeration: 8.0 SL/min; and
Back Pressure: 1 bar.

Substrate Preparation 216 g hexanoic acid diluted in 1,000 g Primol.

After the fermenter was inoculated with the spores, the Primol/hexanoic acid solution was slowly pumped into the fermenter over a 24 hour period. After 51 hours, all the spores were germinated and a total of 1.81 g/l or 13.8 g γ-hexalactone was produced having an optical rotation of +51.7.

EXAMPLE 2

The following medium was prepared in a 14 L fermenter:

Medium 11.8 g/l AMBEREX® 1003;

8.7 g/l Sodium Phosphate, monobasic, $H_2O_2$;

3.9 g/l Sodium Phosphate, dibasic, 7 $H_2O_2$;

7.6 L deionized water;

Sterilized at 121° C. for 20 minutes; and pH adjusted to 6.25 and maintained with 25% NaOH.

Inoculum 20 g MISO TANE KOJI® Spores wetted in 100 ml of YM® media plus 0.1% MAZAWET 36® for 1 hour at 150 RPM before adding to fermenter.

Fermenter Parameters

Temperature: 30° C.;

Agitation: 800 RPM;

Aeration: 8.0 SL/min; and

Back Pressure: 1 bar.

Substrate Preparation 230 g Hexanoic acid diluted in 800 g deionized water adjusted to pH 6.0 and sterilized at 121° C. for 20 minutes.

After the fermenter was inoculated with the spores, the dilute acid solution was slowly pumped into the fermenter over a 24 hour period. After 42.5 hours, all the spores were germinated and an additional 200 g of undiluted acid was pumped into the fermenter at approximately 8.0 g/hr. After 90 hours, a total of 1.3 g/l or 11.6 g γ-hexalactone was produced.

EXAMPLE 3

MISO TANE KOJI® spores were serially diluted and plated for isolated colonies. One isolate was selected for further study and named Aspergillus sp. IFF-8188 (ATCC 74479).

Inoculum Preparation

Medium 5 g/L TASTONE®0900;

10 g/L SOY PEPTONE®;

1.0 g/L MACOL® 2LF;

0.24 g/L Malt Extract;

10 ml/L Trace Mineral Solution:

1.0 g/l $FeSO_4$, $7H_2O$;

1.0 g/L $CaCl_2$, $2H_2O$;

0.05 g/L $CuSO_4$, $5H_2O$;

0.1 g/L $ZnSO_4$, $7H_2O$;

0.1 g/L $MnSO_4$, $H_2O$; and pH adjusted to 6.5 prior to sterilization.

After sterilization: add 0.25% sterile dextrose to flask.

Inoculum

2 Ml of medium was used to wash a slant of Aspergillus sp. IFF-8188 (ATCC 74479), then the wash was used to inoculate 500 ml of media.

Conditions

Temperature: 30° C.;

Agitation: 10 RPM; and

Incubation time: 48 hours.

Production

Nine liters of the inoculum media was prepared in a 14 L fermenter and sterilized at 121° C. for 20 minutes.

Substrate Preparation 232 g Hexanoic acid diluted in 660 g deionized water adjusted to pH 6.0 and sterilized.

Parameters

Temperature: 30° C.;

Agitation: 500 RPM; and

Aeration: 8.0 SL/min.

After sterilization, the fermenter was inoculated with the 48 hour grown fungus culture and 0.25% sterile dextrose was added. After 22 hours of growth, the dilute acid solution was slowly pumped into the fermenter. After 46 hours, undiluted hexanoic acid was pumped into the fermenter. After 118 hours, 1,590 g of hexanoic acid had been pumped into the fermenter and a total of 12.8 g/L γ-hexalactone was produced.

EXAMPLE 4

This experiment was carried out the same as Example 3 except that undiluted hexanoic acid was used as the substrate throughout the fermentation. After 108 hours, 2,381.3 g of hexanoic acid had been pumped into the fermenter and 19.36 g/L γ-hexalactone was produced. During this fermentation a charcoal trap was set up on the fermenter exhaust line. When the charcoal was stripped, 2-pentanone was recovered in excess of 16 g/L.

EXAMPLE 5

This experiment was carried out the same as Example 4, except that the inoculum volume was reduced by half (250 ml) and the initial agitation was set at 500 RPM and initial aeration was set at 4.5 SL/min. The agitation and aeration were returned to their original settings 800 RMP and 8.0 SL/min at the same time that the substrate pumping began. After 114 hours, 1,912.7 g of hexanoic acid had been pumped into the fermenter and 15.2 g/L γ-hexalactone was produced.

EXAMPLE 6

This experiment was the same as Example 5, except that 20% $NH_4OH$ was used to maintain the pH. After 93 hours, 1,677 g of hexanoic acid had been pumped into the fermenter and 7.02 g/L of γ-hexalactone was produced.

EXAMPLE 7

This experiment was the same as Example 5, except that a total of 200 g $CaCO_3$ was added throughout the fermentation to maintain the pH. After 61 hours, 759.3 g of hexanoic acid was pumped into the fermenter and 8.67 g/L γ-hexalactone was produced.

EXAMPLE 8

This experiment was the same as Example 5, except that a different organism, *Aspergillus oryzae* NRRL 3485, was used. After 85.5 hours, 1,232.8 g of hexanoic acid was pumped into the fermenter and a total of 10.8 g/L γ-hexalactone was produced.

EXAMPLE 9

This experiment was the same as Example 5, except that a different organism, *Aspergillus oryzae* NRRL 1731, was used. After 114.5 hours, 907.6 g of hexanoic acid was pumped into the fermenter and a total of 4.5 g/L γ-hexalactone was produced.

EXAMPLE 10

This experiment was the same as Example 5, except that malonic acid was added to the fermenter in order to block lactone consumption by the organism. After 88 hours, 1,265.5 g of hexanoic acid was pumped into the fermenter and 5.5 g/L γ-hexalactone was produced.

EXAMPLE 11

This experiment was carried out the same as Example 5, except that a high level of sugar was maintained throughout the fermentation. After 70.5 hours, 870.3 g of hexanoic acid was pumped into the fermenter and a total of 3.94 g/L γ-hexalactone was produced.

EXAMPLE 12

This was carried out the same as Example 5, except that AMBEREX® 1003 was substituted for TASTONE® 900 and FERMAX® 4000 was substituted for SOY PEPTONE®. After 85.5 hours, 1,509.8 g of hexanoic acid were pumped into the fermenter and a total of 5.2 g/L γ-hexalactone was produced.

EXAMPLE 13

This experiment was carried out the same as Example 12, except that only the inoculum media contained AMBEREX® 1003 and FERMAX® 4000. The fermenter media was not changed. After 69 hours, 1,377.7 g of hexanoic acid was pumped into the fermenter and 8.8 g/L γ-hexalactone was produced.

EXAMPLE 14

This was carried out the same as Example 13, except that 175 g of oleic acid was added during the fermentation in order to block lactone consumption by the organism. After 94 hours, 1,403.5 g of hexanoic acid was pumped into the fermenter and 13.4 g/L γ-hexalactone was produced.

EXAMPLE 15

This was carried out the same as Example 13 except that 0.5 Bar of back pressure was put on the fermenter at the same time that the substrate pumping began. After 68 hours, 726.3 g of hexanoic acid was pumped into the fermenter and 5.29 g/L γ-hexalactone was produced.

EXAMPLE 16

This was carried out the same as Example 13, except that the temperature for both the inoculum and the fermenter was increased to 35° C. After 94 hours, 1,175 g of hexanoic acid was pumped into the fermenter and 9.78 g/L of γ-hexalactone was produced.

EXAMPLE 17

An 800 L fermentation was carried out the same as Example 13. After 48 hours, 57.684 Kg of hexanoic acid had been pumped into the fermenter and a total of 7.50 g/L γ-hexalactone was produced. The product was extracted with ethyl acetate. After removal of the solvent, the crude product as purified using fractional distillation. Final product having purity of 99% and optical rotation of +51.7 with ee% of 98 was obtained.

EXAMPLE 18

A total of ten other fungi were screened for production of γ-hexalactone from hexanoic acid. Of those ten, seven of the organisms were definitely capable of producing γ-hexalactone. These were:

*Aspergillus oryzae* NRRL 2217;

*Aspergillus oryzae* NRRL 2220;

*Aspergillus oryzae* NRRL 1989;

*Aspergillus oryzae* NRRL 3485;

*Aspergillus oryzae* NRRL 3488;

*Aspergillus parasiticus* NRRL 1731; and

*Aspergillus oryzae* NRRL 695.

EXAMPLE 19

A different organism, *Mortierella isabellina* 7873 (CBS 221.29), obtainable from the Institute for Fermentation (IFU) in Osaka, Japan was used in a shake flask experiment for the production of γ-hexalactone.

Inoculum Preparation

One slant of *Mortierella isabellina* 7873 (CBS 221.29) was washed with 5 ml of sterile media and used to inoculate 100 m of media.

Medium 5 g/L TASTONE® 900;

10 g/L SOY PEPTONE®;

0.5 g/L TWEEN® 80;

0.24 G/L Malt Extract;

10 ml/L Trace Mineral Solution:
 1.0 g/l $FeSO_4$, $7H_2O$;
 1.0 g/L $CaCl_2$, $2H_2O$;
 0.05 g/L $CuSO_4$, $5H_2O$;
 0.1 g/L $ZnSO_4$, $7H_2O$;
 0.1 g/L $MnSO_4$, $H_2O$; and pH adjusted to 4.5 prior to sterilization.

After sterilization: Add 0.25% sterile dextrose to flask.

Conditions

Temperature: 27° C.;

Agitation: 150 RPM; and

Incubation time: 72 hours.

Production

Media

Same as inoculum media except pH adjusted to 6.5 prior to sterilization.

Inoculum

A 5% inoculum was used to inoculate 100 ml of production media; and 0.25% sterile dextrose added to flask.

Conditions

Temperature: 27° C.; and

Agitation: 150 RPM.

Incubation time: After 24 hours, 0.15 ml hexanoic acid and 2 g activated carbon were added to the flasks.

Results 24 hours after the substrate was added, 50% of the acid had been converted to γ-hexalactone.

EXAMPLE 20

A 14 L fermenter using *Mortierella isabellina* 7873 (IFO) (CBS 221.29) for the production of γ-hexalactone with activated carbon added to the fermenter.

Inoculum Preparation

One slant of *Mortierella isabellina* 7873 (IFO) (CBS 221.29) was washed with 5 ml of sterile media and used to inoculate 500 ml of media.

Medium 5 g/L TASTONE® 900;

10 g/L SOY PEPTONE®;

0.5 g/L TWEEN® 80;

0.24 g/L Malt Extract;

10 ml/L Trace Mineral Solution:
  1.0 g/l $FeSO_4$, $7H_2O$;
  1.0 g/L $CaCl_2$, $2H_2O$;
  0.05 g/L $CuSO_4$, $5H_2O$;
  0.1 g/L $ZnSO_4$, $7H_2O$;
  0.1 g/L $MnSO_4$, $H_2O$; and
  pH adjusted to 4.5 prior to sterilization.

After sterilization: add 0.25% sterile dextrose to flask.

Conditions

Temperature: 27° C.;

Agitation: 100 RPM; and

Incubation time: 32 hours.

Production

Nine liters of the inoculum media was prepared in a 14 L fermenter, but the pH was adjusted to 6.5 prior to sterilization at 121° C. for 20 minutes.

Parameters

Temperature: 27° C.;

Agitation: 500 RPM; and

Aeration: 1.0 v/v/m.

After sterilization, the fermenter was inoculated with the 32 hour grown fungus culture and 5.0% sterile dextrose was added. After 17 hours of growth, 200 g of activated carbon was added to the fermenter, the hexanoic acid was slowly pumped into the fermenter and the RPM were increased to 600. The dextrose levels were monitored throughout the fermentation and were never allowed to be depleted. After 91.5 hours, 295.3 g of hexanoic acid had been pumped into the fermenter and a total of 6.57 g/L γ-hexalactone was produced. The product was extracted with ethyl acetate. After the removal of the solvent, the crude product was purified using fractional distillation. Final product having a purity of 99% and optical rotation of −39.2 with ee% of 75 was obtained.

EXAMPLE 21

A 14 L fermenter using *Mortierella isabellina* 7873 (IFO) (CBS 221.29) for the production of γ-hexalactone without the addition of activated carbon added to the fermenter and a longer incubation period of the inoculum and initial fermenter growth.

Inoculum Preparation

One slant of *Mortierella isabellina* 7873 (IFO) (CBS 221.29) was washed with 5 ml of sterile media and used to inoculate 500 ml of media.

Medium 5 g/L TASTONE® 900;

10 g/L SOY PEPTONE®;

0.5 g/L TWEEN® 80;

0.24 g/L Malt Extract;

10 ml/L Trace Mineral Solution:
  1.0 g/l $FeSO_4$, $7H_2O$;
  1.0 g/L $CaCl_2$, $2H_2O$;
  0.05 g/L $CuSO_4$, $5H_2O$;
  0.1 g/L $ZnSO_4$, $7H_2O$;
  0.1 g/L $MnSO_4$, $H_2O$; and
  pH adjusted to 4.5 prior to sterilization.

After sterilization: add 0.25% sterile dextrose to flask.

Conditions

Temperature: 27° C.;

Agitation: 100 RPM; and

Incubation time: 67 hours.

Production

Nine liters of the inoculum media was prepared in a 14 L fermenter, but adjusted to 6.5 prior to sterilization at 121° C. for 20 minutes.

Parameters

Temperature: 27° C.;

Agitation: 600 RPM;

Aeration: 1.0 v/v/m;

After sterilization, the fermenter was inoculated with the 67 hours grown fungus culture and 5.0% sterile dextrose was added. After 21.5 hours of growth, the hexanoic acid was slowly pumped into the fermenter. The dextrose levels were monitored throughout the fermentation and were never allowed to be depleted. After 100.5 hours, 477 g of hexanoic acid had been pumped into the fermenter and a total of 9.56 g/L γ-hexalactone was produced.

EXAMPLE 22

Composition of Media for γ-hexalactone Production.

Production

Ingredient g/L

Amberex 5500 14.82;

$NaH_2PO_4$ 10.80;

$Na_2HPO_4$ 3.46;

Na hexametaphosphate 14.78; and

DI Water 1,000.

Production Fermenter 8 liters of media was prepared in a 20 liter fermenter and the pH was adjusted to 6.0. Super LA 35 USP mineral oil at a quantity of 454 g/L of media was added to the fermenter. The mixture was heated at 110° C. for 1 hour, and then cooled to 30° C. A total of 24 g MISO TANE KOJI® spores were dispersed in 100 ml sterile water and added to the fermenter. The exhaust was connected to a carbon trap containing 300 grams of activated carbon to trap the volatile 2-pentanone formed during the conversion. The trap was replaced once it was saturated with the ketone.

Fermenter Parameters

Agitation: 400 rpm;

Aeration: 0.5 v/v/m;

Back pressure: 15 psi;

Temperature: 30° C.;

Duration: 27.5 hours; and pH was controlled at 6.0 using 25% sodium hydroxide.

Hexanoic acid feed

A total of 388 grams of hexanoic acid was fed into fermenter at a rate 0.02 to 0.13% per hour calculated based on the amount of media. The hexanoic acid level was maintained below 2.5 g/L.

Termination

After termination, the γ-hexalactone level was measured as 3.3 g/L with GC method. A total of 600 grams of carbon was used for trapping 2-pentanone. At the end of fermentation, the total carbon weight was 740 grams. The carbon was mixed with 925 grams of water and steam distilled. A total of 52.23 grams of 2-pentanone with an average of purity of 99.3% was recovered.

EXAMPLE 23

The same media composition as in Example 22 was used. This experiment was a shake flask study with pH of the media adjusted to 4.0, 5.0, 6.0, 7.0, 8.0 and 9.0. All flasks were sterilized at 121° C. for 25 minutes. Each 500 ml flask contained 100 ml of media and 0.5 grams of MISO TANE KOJI® spores which was dispersed in 5 ml of sterile water and added to each flask. A 28% hexanoic acid solution in the form of sodium hexanoate at pH 6.6 was prepared and used as the feed material. 100 to 600 Microliters of feed material was added to each flask every one to five hours. At the end, a total of 6.4 gram hexanoic acid per liter media was added to each flask.

Parameters

Agitation: 200 rpm;

Temperature: 30° C.; and

Duration: 29 hours.

Termination

At 29 hours, each flask was acidified to a pH of 2.0 with concentrated sulfuric acid and boiled for 5 minutes under reflux. Both the aqueous and oil phase were analyzed for 2-pentanone, γ-hexalactone and hexanoic acid content using the GC method. The result (mg/ml) were:

| pH | 2-Pentanone | γ-Hexalactone | Hexanoic acid |
| --- | --- | --- | --- |
| 4.0; aqueous | — | — | 4.796 |
| 4.0; oil | — | — | 5.217 |
| 5.0; aqueous | — | — | 4.706 |
| 5.0; oil | — | — | 3.842 |
| 6.0; aqueous | 1.405 | 0.601 | 0.662 |
| 6.0; oil | 3.890 | 0.14 | 1.597 |
| 7.0; aqueous | 0.862 | 0.377 | 0.800 |
| 7.0; oil | 3.045 | — | 1.596 |
| 8.0; aqueous | 0.931 | 0.463 | 1.055 |
| 8.0; oil | 2.642 | — | 1.396 |
| 9.0; aqueous | 0.182 | 0.121 | 3.871 |
| 9.0; oil | 0.210 | — | 4.828 |

EXAMPLE 24

Example 24 was identical to Example 23 at a pH of 60, except no mineral oil was used. The amount of hexanoic acid fed and the feeding time were also identical. After termination, both were acidified to a pH 2.0 with concentrated sulfuric acid and boiled for 5 minutes with a reflux condenser. The 2-pentanone content in the broth was 2.69 mg/ml. The γ-hexalactone content in broth was 0.838 mg/ml. No residual hexanoic acid was found.

The following examples illustrate the use of the compounds of this invention as components in various compositions to augment or enhance those compositions.

EXAMPLE 25

The following mixture is prepared:

TABLE I

| Ingredients | Parts by Weight |
| --- | --- |
| Orange oil | 50 |
| Bergamot oil | 20 |

TABLE I-continued

| Ingredients | Parts by Weight |
| --- | --- |
| Lime oil | 100 |
| Neroli oil | 5 |
| 4-(4-Methyl-4-hydroxymethyl)δ-cyclohexene carboxaldehyde | 5 |
| 2.3.3A,4,5,7A-Hexahydro-6,7A.8.8-tetramethyl-1.5,methano-1H-inden-1-ol (prepared according to the process of Example 1 of U.S. Pat. No. 3,989,760 | 100 |
| 1',2',3',4',5',6',7',8',-Ocathydro 2',3',8',8'-tetramethyl-2'acetonaphthone isomer mixture produced according to the process of Example VII of U.S. Pat. No. 3,911,018 | 50 |
| γ-Methyl ionone | 20 |
| 1-Acetyl-2,5,5-trimethylcycloheptane produced according to U.S. Pat. No. 3,869,411 | 50 |
| Compound prepared according to Example 1 | 150 |

The compound prepared according to Example 1 adds to this pactchouli formulation a sophisticated, sweet, fruity, peach-like aroma profile with green and herbaceous topnotes.

EXAMPLE 26

Preparation of Soap Compositions

100 Grams of soap chips are produced according to Example V of U.S. Pat. No. 4,058,487, the specification for which is incorporated herein by reference as follows:

The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated coconut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 pounds of water, 0.2 pounds of titanium hydroxide and 0.7 pounds of one of the perfume ingredients set forth in Table II below. The chips are then plodded into logs, cut to size and finally stamped into bars having a pH of approximately 6.9.

The perfume soap produced by means of the foregoing procedure manifests an excellent aroma as set forth in Table II, infra:

TABLE II

| Ingredient | Fragrance Profile |
| --- | --- |
| Compound produced according to Example 1. | A peach aroma. |
| Perfume composition of Example 25. | A patchouli aroma with peach-like undertones and herbaceous topnotes. |

EXAMPLE 27

Preparation of a Detergent Composition

A total of 100 grams of a detergent powder prepared according to U.S. Pat. No. 4,058,472 (the specification for which is incorporated by reference herein) and containing 5% by $C_{14}$–$C_{18}$ alkyl catechol as a surface active component, the mixture being 60 parts by weight of mono-$C_{14}$–$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with the aroma ingredient set forth in Table II of Example 26 until a substantially homogeneous composition is obtained. The composition has an excellent aroma as set forth in Table II of Example 26.

EXAMPLE 28

Preparation of a Cosmetic Powder Composition

A cosmetic powder is prepared by mixing in a ball mill, 100 grams of talcum powder with 0.25 grams of the perfume material of Table II of Example 26. The powder has an excellent aroma as set forth in Table II of Example 26.

EXAMPLE 29

Perfumed Liquid Detergent

Concentrated liquid detergents with aromas as set forth in Table II of Example 26 are prepared by adding 0.10%, 0.15% and 0.20% of the ingredient set forth in Table II of Example 26. They are prepared by adding and homogeneously mixing the appropriate quantity of perfume substance of Table II of Example 26 in the liquid detergent. The detergents individually possess aromas as set forth in Table II of Example 26, the intensity increasing with greater concentration of perfume substances set forth in Table II of Example 26.

EXAMPLE 30

Preparation of a Cologne Handkerchief Perfume

The ingredient of Table II of Example 26 is incorporated into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table II of Example 26 are imparted to the colognes and to the handkerchief perfumes at the several concentrations set forth above.

EXAMPLE 31

Preparation of Soap Compositions

100 Grams of soap chips (IVORY® produced by the Proctor & Gamble Company of Cincinnati, Ohio) are admixed with one gram of the substance set forth in Table II of Example 26, supra, until homogenous compositions are obtained. The homogeneous composition is heated under 3 atmospheres pressure at 180° C. for a period of three hours and the resulting liquid is placed into soap molds. The resulting soap cakes, on cooling, manifest excellent aromas as set forth in Table II of Example 26.

EXAMPLE 32

| PREPARATION OF SOLID DETERGENT COMPOSITIONS Detergents are prepared from the following ingredients according to Example I of Canadian Patent No. 1,007,948, the specification for which is incorporated by reference herein: | |
|---|---|
| Ingredients | Parts by Weight |
| NEODO1 ® 45-11 (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

The detergent is a "phosphate-free" detergent. A total of 100 grams of said detergent is admixed with 0.10, 0.15, 0.20 and 0.25 grams of the substance set forth in Table II of Example 26, supra. Each of the detergent samples has an excellent aroma as indicated in Table II of Example 26.

EXAMPLE 33

Preparation of Drier-Added Fabric Softner Article

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:

1. a water "dissolvable" paper ("Dissolve Paper") as the substrate.
2. ADOGEN® 448 (melting point about 140° F.) as the first substrate coating; and
3. an outer coating having the following formulation (melting point about 150° F.):
   57% $C_{20}$–$C_{22}$ HAPS;
   22% isopropyl alcohol;
   20% antistatic agent
   1% of the perfumery substance set forth in Table II of Example 26, supra.

Fabric softening compositions containing the substance as set forth in Table II of Example 26, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table II of Example 26, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. Patent may be perfumed in their outer coating with from 0.25% up to 5% by weight of the perfuming substance of Table II of Example 26, supra.

EXAMPLE 34

| HAIR PREPARATION A "soft-feel, good-hold" hair spray is produced containing the following ingredients: ||
|---|---|
| Ingredients | Parts by Weight |
| Polyvinylpyrollidone/vinyl acetate "E-735 Copolymer" manufactured by the Corporation of New York, NY | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, NY | 24.95 |
| Fragrance ingredient as set forth in Table II of Example 26, supra | 0.05 |

The PVP/VA copolymers are first dissolved in alcohol and all other ingredients are added until uniform. The propellant is then pressurized and used as an aerosol. The resulting hair sprays each have pleasant aromas as set forth in Table II of Example 26.

EXAMPLE 35

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substance set forth in Table II of Example 26, supra, is added at the level of 0.025% as set forth in the table in said Example I of U.S. Pat. No. 4,193,888 yielding an aroma on using said cleanser in ordinary circumstances which is quite pleasant and described in Table II of Example 26, supra.

EXAMPLE 36

A fabric softening article prepared substantially as set forth in Example VII of Canadian Patent No. 1,069,260, the specification for which is incorporated by reference herein, is prepared containing 0.21% by weight of a perfuming substance as set forth in Table II of Example 26, supra, and yielding on use in a drier, a faint aroma as set forth in Table II of Example 26, supra.

EXAMPLE 37

Pudding

At the rate of 0.8 ppm the mixture compound produced according to Example 1 is added to a ROYAL® Butterscotch Pudding. Pleasant aesthetically pleasing peach nuances were added to the butterscotch pudding with the panel of 30 members preferring the butterscotch pudding with the mixture of compounds added thereto than a butterscotch pudding without the mixture of compounds added thereto.

EXAMPLE 38

Flavor Formulations

| Ingredient | Parts by Weight |
|---|---|
| Compound defined according to the structure: 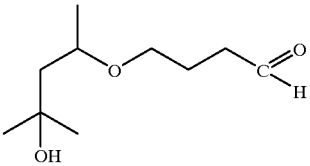 prepared according to Example VI of U.S. Pat. No. 4,532,364. | 26.0 |
| The compound mixture produced according to Example 1 | 12.0 |
| Natural lemon oil terpeneless | 10.0 |
| Acetaldehyde | 0.6 |
| α-Terpineol | 2.1 |
| Citral | 1.8 |
| Carvone | 0.24 |
| Terpinolene | 1.2 |
| α-terpinene | 0.25 |
| Diphenyl | 0.25 |
| α-Fenchyl alcohol | 0.25 |
| Limonene | 0.35 |
| Linalool | 0.25 |
| Geranyl acetate | 0.25 |
| Nootkatone | 0.25 |
| Neryl acetate | 0.25 |

The flavor formulation with the lactone of Example 1 has a definite natural rich orange aroma with buttery nuances due to the addition of the buttery principals to this citrus flavor.

EXAMPLE 39

A. Powder Flavor Compositions

20 Grams of the flavor composition of Example 38 containing the compound of Example 1 is emulsified in a solution containing 300 grams gum acacia and 700 grams water. The emulsions are spray-dried with a Bowen Lab Model Drier utilizing 260 c.f.m. of air with an inlet temperature of 500° F., an outlet temperature of 200° F., and a wheel speed of 50,000 rpm.

| B. SUSTAINED RELEASE FLAVOR ||
|---|---|
| Ingredients | Parts by Weight |
| Liquid Citrus Flavor Compositions of Example 38 | 20.0 |
| Propylene glycol | 9.0 |
| CAB-O-SIL ® M-5 (Brand of Silica produced by the Coat Corporation of 125 High Street, Boston, MA 0210): Physical Properties: | 5.0 |
| Surface area: 200 m₂/gm Nominal particle size: 0.012 microns Density: 2.3 lbs/cu.ft.) | |

The CAB-O-SIL® is dispersed in the liquid citrus flavor compositions of Example 38 with vigorous stirring, thereby resulting in each case in a viscous liquid. 71 Parts by weight of the powder flavor compositions of Part "A," supra, are then separately blended into the said viscous liquids, with stirring, at 25° C. for a period of 30 minutes resulting in dry, free flowing sustained release flavor powder.

EXAMPLE 40

10 Parts by weight of 50 Bloom pigskin gelatin is added to 90 parts by weight of water at a temperature of 150° F. The mixture is agitated until the gelatin is completely dissolved and the solution is cooled to 120° F. Separately, 20 parts by weight of the liquid flavor composition of Example 39 is added to the solution which is then homogenized to form an emulsion having particle size typically in the range of 5–40 microns. This material is kept at 120° F. Under which conditions the gelatin will not jell.

Coacervation is induced by adding, slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixtures into 1,000 parts by weight (each) of 7% aqueous solutions of sodium sulphate at 65° C. The resulting jelled coacervates may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE 41

Chewing Gum

100 Parts by weight of chicle are mixed with 4 parts by weight of the flavor prepared in accordance with Example 39B. 300 Parts of sucrose and 100 parts of corn syrup are added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long-lasting rich citrus flavor.

EXAMPLE 42

Chewing Gum

100 Parts by weight of chicle are mixed with 18 parts by weight of each of the flavors prepared in accordance with Example 39B. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gums has a pleasant, long-lasting rich citrus flavor.

EXAMPLE 43

Toothpaste Formulation

The following separate groups of ingredients are prepared:

| Ingredients | Parts by Weight |
| --- | --- |
| Group "A" | |
| Glycerine | 30.200 |
| Distilled water | 15.325 |
| Sodium benzoate | 0.100 |
| Saccharin sodium | 0.125 |
| Stannous fluoride | 0.400 |
| Group "B" | |
| Calcium carbonate | 12.500 |
| Dicalcium phosphate (dihydrate) | 37.200 |
| Group "C" | |
| Sodium N-lauroyl sarcoginate (foaming agent) | 2.000 |
| Group "D" | |
| Flavor materials of Example 39B | 1.200 |

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, the flavor "D" is added and lastly the sodium n-lauroyl sarcosinate; and
5. The resultant slurry is then blended for one hour. The completed paste is then transferred to a three roller mill and then homogenized, and finally tubed.

The resulting toothpastes when used in normal toothbrushing procedures yield pleasant rich citrus flavors, of constant strong intensity throughout said procedure (1–1.5 minutes).

EXAMPLE 44

Chewable Vitamin Tablets

The flavor materials produced according to the process of Example 39 is added to a chewable vitamin tablet formulation at a rate of 10 gm/Kg which chewable vitamin tablet formulation is prepared as follows:

In a Hobart Mixer the following materials are blended to homogeneity:

| Ingredients | Gms/1,000 Tablets |
| --- | --- |
| Vitamin C (ascorbic acid) as ascorbicacid-sodium ascorbate mixture 1:1 | 70.0 |
| Vitamin $B_1$ (thiamine mononitrate) as ROCOAT ® thiamine mononitrate 33 ⅓ (Hoffman La Roche) | 4.0 |
| Vitamin $B_2$ (riboflavin) as ROCOAT ® riboflavin 33 ⅓% | 5.0 |
| Vitamin $B_6$ (pyridoxine hydrochloride) as ROCOAT ® pyridoxine hydrochloride 33 ⅓% | 4.0 |

-continued

| Ingredients | Gms/1,000 Tablets |
| --- | --- |
| Niacinamide as ROCOAT ® niacinamide 33 1/3% | 33.0 |
| Calcium pantothenate | 11.5 |
| Vitamin $B_{12}$ (cyanocobalamin) (Merck) 0.1% in gelatin | 3.5 |
| Vitamin E (dl-alpha tocopheryl acetate) as dry Vitamin E acetate 33 1/3% Roche | 6.6 |
| d-Biotin | 0.004 |
| One of the Flavors of Example 39 | (as indicated above) |
| Certified lake color | 5.0 |
| Sweetener - sodium saccharin | 1.0 |
| Magnesium stearate lubricant | 10.0 |
| Mannitol | (q.s. to make) 500.0 |

Preliminary tablets are prepared by slugging with flat-faced punches and grinding the slugs to 14 mesh. 13.6 G dry Vitamin A acetate and 0.6 g Vitamin D are then added as beadlets. The entire blend is then compressed using concave punches at 0.5 g each.

Chewing of the resultant tablets yields pleasant, long-lasting, consistently strong rich citrus flavors for a period of 12 minutes.

EXAMPLE 45

To 100 parts by weight of GOYA® mango nectar (produced by the Goya Corporation of New York, N.Y.) is added 10 ppm of the lactone produced according to Example 1. The lactone mixture adds to the mango nectar a very natural nuance which although present in natural mango (prior to adding the lactone of Example 1) is lost in the canning process when the mango nectar is prepared and canned in the usual manner.

We claim:
1. A process for the production of γ-hexalactone represented by the structural formula:

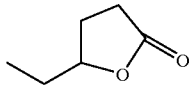

comprising the steps of preparing an aqueous nutrient medium as a first aqueous liquid phase, preparing as a second phase hexanoic acid having the formula:

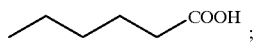

mixing said first aqueous phase and said second phase together with agitation to form a reaction medium, aerating with an oxygen containing gas in a sufficient amount to maintain oxidative conditions to thereby achieve an oxidation reaction in the presence of a fungus capable of producing said natural γ-hexalactone which fungus is a member selected from the group consisting of Aspergillus and Mortierella.

2. The process according to claim 1 wherein said fungus is a member selected from the groups consisting of:
*Aspergillus oryzae* NRRL 2217
*Aspergillus oryzae* NRRL 2220
*Aspergillus oryzae* NRRL 1989
*Aspergillus oryzae* NRRL 3485
*Aspergillus oryzae* NRRL 3488
*Aspergillus parasiticus* NRRL 1731
*Aspergillus oryzae* NRRL 695
Aspergillus sp. IFF-8188 (ATCC 74479); and
*Mortierella isabellina* 7873 (CBS 221.29).

3. The process according to claim 1 further comprising recovery of γ-hexalactone and 2-pentanone.

4. The process according to claim 1 wherein a diluent is present with the hexanoic acid.

5. The process according to claim 1 wherein said nutrient medium is fed into said reaction medium at a rate sufficient to enable said fungus to maintain oxidative growth and thereby generate said compound.

6. The process according to claim 1 wherein the aeration is delivered at a rate enabling interaction with said nutrient to avoid production of unwanted compounds.

7. The process according to claim 6 wherein oxidative conditions are maintained throughout the reaction.

8. A composition produced by the process according to claim 1 and having a profile corresponding to FIG. 1.

9. A composition produced by the process according to claim 1 and having a profile corresponding to FIG. 2.

10. A composition produced by the process according to claim 1 and having a profile corresponding to FIG. 3.

11. A composition produced by the process according to claim 1 and having a profile corresponding to FIG. 4.

12. A composition produced by the process according to claim 1 and having a profile corresponding to FIG. 5.

13. A composition produced by the process according to claim 1 and having a profile corresponding to FIG. 6.

14. A fragrance composition consisting essentially of a fragrance base and intimately admixed therewith an aroma augmenting, enhancing or imparting quantity and concentration of the composition defined according to claim 8.

15. A fragrance composition consisting essentially of a fragrance base and intimately admixed therewith an aroma augmenting, enhancing or imparting quantity and concentration of the composition defined according to claim 9.

16. A fragrance composition consisting essentially of a fragrance base and intimately admixed therewith an aroma augmenting, enhancing or imparting quantity and concentration of the composition defined according to claim 10.

17. A fragrance composition consisting essentially of a fragrance base and intimately admixed therewith an aroma augmenting, enhancing or imparting quantity and concentration of the composition defined according to claim 11.

18. A fragrance composition consisting essentially of a fragrance base and intimately admixed therewith an aroma augmenting, enhancing or imparting quantity and concentration of the composition defined according to claim 12.

19. A fragrance composition consisting essentially of a fragrance base and intimately admixed therewith an aroma augmenting, enhancing or imparting quantity and concentration of the composition defined according to claim 13.

20. A foodstuff composition consisting essentially of a foodstuff base and intimately admixed therein a flavor augmenting, enhancing or imparting quantity and concentration of the composition defined according to claim 8.

21. A foodstuff composition consisting essentially of a foodstuff base and intimately admixed therein a flavor augmenting, enhancing or imparting quantity and concentration of the composition defined according to claim 9.

22. A foodstuff composition consisting essentially of a foodstuff base and intimately admixed therein a flavor augmenting, enhancing or imparting quantity and concentration of the composition defined according to claim 10.

23. A foodstuff composition consisting essentially of a foodstuff base and intimately admixed therein a flavor augmenting, enhancing or imparting quantity and concentration of the composition defined according to claim 11.

24. A foodstuff composition consisting essentially of a foodstuff base and intimately admixed therein a flavor augmenting, enhancing or imparting quantity and concentration of the composition defined according to claim 12.

25. A foodstuff composition consisting essentially of a foodstuff base and intimately admixed therein a flavor augmenting, enhancing or imparting quantity and concentration of the composition defined according to claim 13.

26. A cologne composition comprising water, ethanol and an aroma augmenting, enhancing or imparting quantity and concentration of the composition defined according to claim 8.

27. A process for augmenting, enhancing or imparting an aroma or taste in or to a consumable material selected from the group consisting of foodstuffs, fragrances and chewing gum comprising intimately admixing an aroma or taste augmenting, enhancing or imparting amount and concentration of the composition defined according to claim 8.

* * * * *